United States Patent
Mamo et al.

(10) Patent No.: US 12,239,569 B2
(45) Date of Patent: Mar. 4, 2025

(54) CATAMENIAL FLUID REMOVAL

(71) Applicant: PERRYDIGMA RESEARCH LTD., Tel Aviv (IL)

(72) Inventors: Shay Joseph Mamo, Ramat HaSharon (IL); Ran S. Sopher, Ramat Gan (IL); Michal Stern-Perry, Ramat Hasharon (IL)

(73) Assignee: PERRYDIGMA RESEARCH LTD., Ramat Hasharon (IL)

( * ) Notice: Subject to any disclaimer, the term of this patent is extended or adjusted under 35 U.S.C. 154(b) by 1002 days.

(21) Appl. No.: 17/281,101

(22) PCT Filed: Oct. 7, 2019

(86) PCT No.: PCT/IL2019/051090
§ 371 (c)(1),
(2) Date: Mar. 29, 2021

(87) PCT Pub. No.: WO2020/079677
PCT Pub. Date: Apr. 23, 2020

(65) Prior Publication Data
US 2021/0338474 A1    Nov. 4, 2021

(30) Foreign Application Priority Data
Oct. 17, 2018 (IL) .......................... 262450

(51) Int. Cl.
*A61F 5/455* (2006.01)
*A61M 1/00* (2006.01)

(52) U.S. Cl.
CPC ............ *A61F 5/4553* (2013.01); *A61M 1/76* (2021.05); *A61M 1/87* (2021.05);
(Continued)

(58) Field of Classification Search
CPC ....... A61F 5/4553; A61F 5/4405; A61M 1/76; A61M 1/87; A61M 2202/0413;
(Continued)

(56) References Cited

U.S. PATENT DOCUMENTS 1,926,900 A   9/1933   Haas
3,774,612 A   11/1973  Marco
(Continued)

FOREIGN PATENT DOCUMENTS

CN   1354647 A     6/2002
CN   101389301 A   3/2009
(Continued)

OTHER PUBLICATIONS

Communication from a China patent office in a counterpart China application—No. 201980068273.0—mailed Dec. 22, 2022 (10 pages); and English translation (10 pages).
(Continued)

*Primary Examiner* — William R Carpenter
(74) *Attorney, Agent, or Firm* — Roach Brown McCarthy & Gruber, P.C.; Kevin D. McCarthy

(57) ABSTRACT

The invention provides a device for aspirating uterine fluid of a woman in her period, enabling her, without using tampons, pads or synthetic hormones, to be free of menstrual flow for six or more hours and to be involved in even the most demanding activities entirely undisturbed.

13 Claims, 21 Drawing Sheets

(52) U.S. Cl.
CPC ............... *A61M 2202/0413* (2013.01); *A61M 2210/1433* (2013.01); *A61M 2210/1475* (2013.01)

(58) Field of Classification Search
CPC .. A61M 2210/1433; A61M 2210/1475; A61M 2205/058; A61M 2205/3306; A61M 2205/3334; A61M 2205/3351; A61M 1/75; A61M 1/84; A61M 1/74; A61M 1/80; A61M 1/88; A61M 29/00; A61B 2017/00411; A61B 1/32; A61B 17/22; A61B 17/42; A61N 7/00; A61N 2007/0043

See application file for complete search history.

(56) References Cited

U.S. PATENT DOCUMENTS

| | | | |
|---|---|---|---|
| 3,860,001 | A | 1/1975 | Levin |
| 4,141,360 | A | 2/1979 | Lasswell |
| 4,955,875 | A | 9/1990 | Knowles |
| 5,485,853 | A | 1/1996 | Stubbs |
| 5,782,779 | A | 7/1998 | Kilgore |
| 6,090,038 | A | 7/2000 | Zunker et al. |
| 8,171,575 | B2 | 5/2012 | Oh |
| 9,731,063 | B2 | 8/2017 | Shin et al. |
| 10,398,591 | B2 | 9/2019 | Feemster et al. |
| 10,722,622 | B2 | 7/2020 | Loske |
| 2010/0056963 | A1* | 3/2010 | Shaviv ............... A61H 23/0218 604/385.01 |
| 2013/0245637 | A1* | 9/2013 | Norred .................. A61B 17/42 606/119 |
| 2014/0378750 | A1* | 12/2014 | Buster ................... A61B 17/42 600/33 |
| 2024/0207085 | A1* | 6/2024 | Mugadza .............. A61F 5/4553 |

FOREIGN PATENT DOCUMENTS

| | | |
|---|---|---|
| CN | 101583328 A | 11/2009 |
| CN | 102805660 A | 12/2012 |
| CN | 106488748 A | 3/2017 |
| CN | 108210152 A | 6/2018 |
| JP | 2013-526949 A | 5/2011 |
| WO | 2008144871 A2 | 12/2008 |
| WO | 2012/137894 A1 | 10/2012 |

OTHER PUBLICATIONS

Communication and Supplementary European Search Report, mailed Jun. 8, 2022 (8 pages).

Japanese office action for application No. 2021-520596 mailed on Jun. 29, 2023 (6 pages); English machine translation (6 pages).

Chinese office action of corresponding Chinese Patent application No. 201980068273.0 transmitted on Jul. 26, 2023 (9 pages); and English machine translation (10 pages).

International Search Report for PCT/IL2019/051090, mailed on Dec. 25, 2019 (3 pages).

Written Opinion of the International Searching Authority for PCT/IL2019/051090, mailed on Dec. 25, 2019 (8 pages).

* cited by examiner

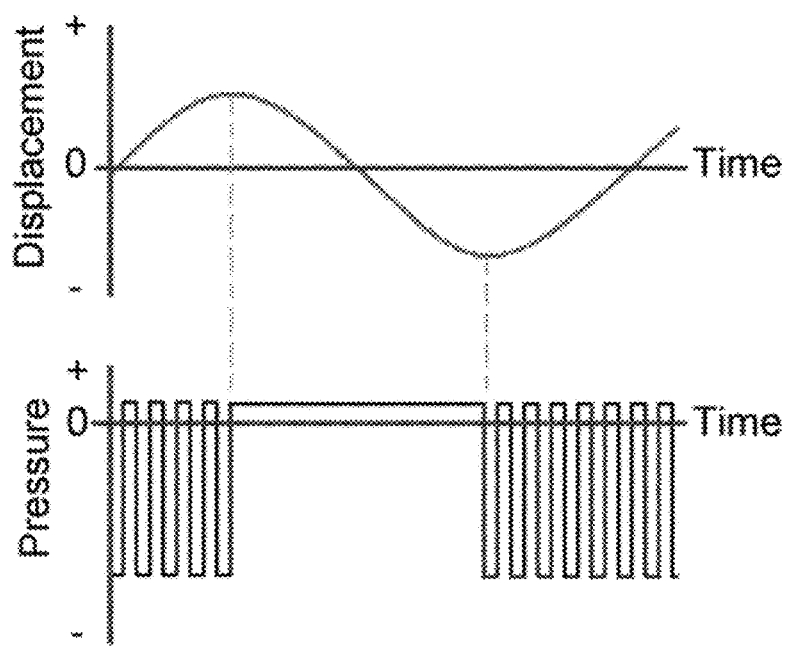
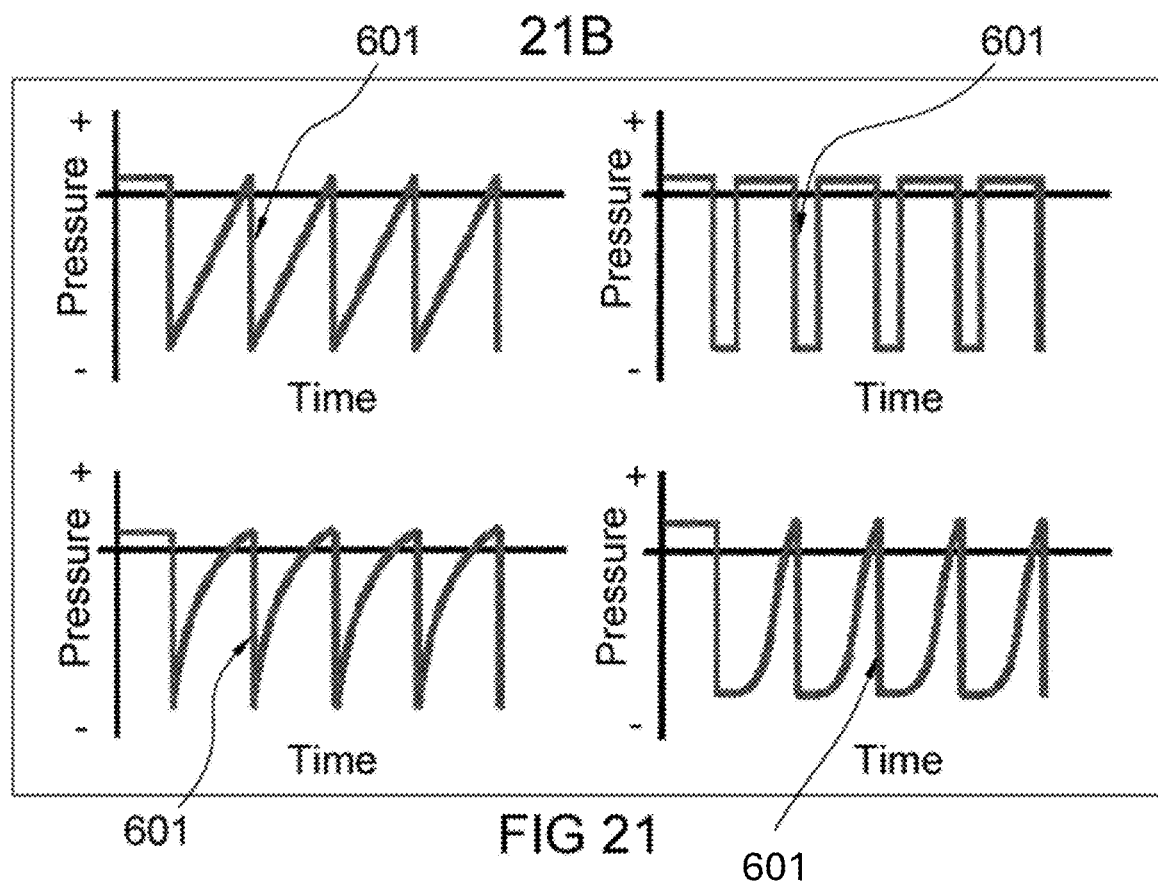
FIG 21

CATAMENIAL FLUID REMOVAL

The present invention relates to menstrual management, and particularly to a device which simplifies daily planning to a woman going through her menstruation. More particularly, the invention relates to a device which reduces the need for tampons, pads, or synthetic hormones, while providing the user with predetermined time intervals without menstrual discharge.

BACKGROUND OF THE INVENTION

The women's monthly hormonal cycle is associated with fluid discharge from the inner lining of the uterus (endometrium) through the vagina. The duration of menstrual bleeding normally ranges between 2 to 7 days. The total volume of monthly menses normally ranges between 20 to 120 ml, wherein blood constitutes approximately half of the fluid and aqueous salts with tissue shreds constitute the other half. Menstruation normally occurs from the age of 13 through the age of 50, covering approximately half of a woman's life. An average menstrual cycle of 28 days naturally directed people's attention to the lunar cycle and astral connections. This phenomenon, associated with women's fertility, has contributed to the struggle of women in acquiring equal status with men. The practices of menstrual management throughout history have included attempts to absorb the fluids, wearing special garments, disposal of stained materials, washing, separation of women, and in modern times employing feminine hygiene products or suppression of menstruation by synthetic hormones.

The menstrual cycle not only causes inconvenience and discomfort, but is also often associated with emotional disturbances, which, in some cases, may be quite severe. Moreover, the existing means for managing menses do not always solve the problems, and sometimes even cause serious complications. For example, the use of tampons may result in toxic shock syndrome; the use of synthetic hormones is sometimes not recommended, and in some conditions it is even contraindicated. Moreover, there is always a possibility of unexpected timing or volume of the discharge, which may bear embarrassing and uncomfortable consequences. Western society exerts strong efforts to remove any handicaps that might prevent women from enjoying equal rights and achieving equal status. Therefore, a need is felt to provide new means for managing menses during the menstrual cycle and preventing inconvenience.

Besides simply employing absorption textiles, various devices have been suggested; some try to block the discharge from vagina, others from cervix, including intravaginal inflating members. Various draining apparatuses and collecting means have been described. Many devices, while being rather cumbersome, only passively transfer or collect fluids. It is therefore an object of the invention to provide a device avoiding the drawbacks of the known devices.

Since women nowadays occupy most demanding positions, including in hospitals, in high management, in high performance sport, and even in combat situations, it is necessary to ensure at least several hours free of menstrual flow, preferably six or more hours, without the need to care for anything other than working matters. Attempts have appeared to aspirate the fluid out of the vagina or facilitate the flow from the uterus. It is an object of the invention to provide a device enabling to adjust the rate, duration and timing of the menstrual flow.

It is another object of this invention to provide a system allowing a woman in her menstrual period to better plan her activities and avoid inconvenient and embarrassing moments.

It is a further object of this invention to provide a system enabling a reduced usage of tampons and pads.

It is still another object of this invention to provide a system ensuring that the menstrual flow is collected in predetermined times.

This invention aims at providing a system ensuring predetermined time intervals free of menstrual flow. This invention also aims at providing a device for collecting the menstrual flow in predetermined times and providing the user with time intervals free of menstrual flow.

Other objects and advantages of the present invention will appear as the description proceeds.

SUMMARY OF THE INVENTION

The invention provides a device for aspirating uterine fluid, comprising: i) a vacuum pump; ii) a suction tube having a first and a second end, connected with said pump via said first end, with at least a part of the tube defining a linear axis; iii) a suction cup connected with said tube via said second end and being wider than said tube, comprising an opening for aspirating said fluid, the cup and the tube being configured to be inserted into the human vagina; iv) a noninvasive cervix-opening means; v) a liquid trap connected between said pump and said suction tube for holding said fluid; and vi) a processor for controlling the performance of said pump and said noninvasive cervix-opening means, and for storing software determining the device working regimen. Said cervix-opening means and said processor preferably comprises a vacuum regulation means which provide sudden application of vacuum, thereby aspirating the vaginal and uterine fluid; the regulation means preferably create vacuum oscillations, for example by alternatingly connecting and disconnecting said pump with said cup, with a frequency of between 1 to 25 Hz, such as 1 to 15 Hz or 4 to 15. The vacuum regulation means may comprise a valve or a diaphragm pump, for example similar to breast pumps, or other suitable means. Said cervix-opening means comprises, in a preferred embodiment of the invention, an apparatus allowing a translational movement of said tube and said cup along said axis in both directions up to 40 mm, up to 20 mm in each direction, comprising an engine and an attachment member for connecting said suction tube with said engine, wherein said cup is made of a medical grade elastomer. Said cervix-opening means in the device of the invention comprises, in another embodiment, an apparatus supplying vibrations to the cervix during the vacuum aspiration. Said vacuum regulation means, providing sudden application of vacuum, preferably provide vacuum oscillations in the form of square waves or sawtooth waves. In one embodiment, the device of the invention comprises an apparatus supplying acoustic waves to the cervix. Said cervix-opening means may combine two or three of the following: vacuum oscillations, translational movement of the cup in contact with the cervix, and vibrations supplied to the cervix. Said processor preferably controls also said engine. In one embodiment, the device of the invention comprises one or more pressure sensors. Said processor preferably receives data from said sensors. Said cup is preferably made of a medical-grade elastomer and comprises a surface being convex on the side of said suction tube. The cup and the tube are smooth, without any sharp or irritating elements. Said suction tube and said cup are configured to adhere to the cervix, while aspirating said fluid. The device preferably comprises a means for cutting blood clots or tissue shreds eventually present in said uterine fluid to smaller pieces before they enter to said suction tube. The suction tube and the cup are configured to be inserted into the human vagina and to dock with the cervix, while aspirating said fluid. Said translational movement results in said cup moving up to 20 mm towards the cervix and 20 mm away from the cervix, which results in displacement of said cervix. Said pump preferably provides a maximal vacuum pressure (negative pressure) of between −150 and −800 mbar gauge, and a maximal positive pressure of between 20 and 200 mbar gauge.

The invention is directed to a device for use in removing uterine and vaginal fluid during menses, resulting in at least one of the following effects: providing the user with predetermined time intervals without menstrual discharge, reducing the overall volume of the monthly menstrual discharge, reducing the duration of menstrual bleeding, reducing menstrual cramps, reducing menstrual pain, and reducing the need for tampons and pads.

The invention provides a method of aspirating uterine fluid, comprising: i) providing a suction cup made of a medical grade polymer, and a suction tube having a first end connected with a vacuum pump and a second end connected with said cup, at least a part of the tube defining a linear axis, the cup comprising an opening for aspirating said fluid; ii) providing a noninvasive cervix-opening means selected from (a) a vacuum-regulation means connecting and disconnecting said vacuum pump with said cup with a frequency of between 1 and 15 Hz, thereby providing oscillating vacuum to said cup, (b) an apparatus allowing a translational movement of said cup along said axis in both directions, thereby pushing and pulling said cup within a total distance of up to 40 mm, (c) an apparatus supplying vibrations to the cervix during the vacuum aspiration, or (d) a combination thereof; iii) inserting said cup into the vagina so it is adjacent to the cervix; iv) activating said cervix-opening means, wherein said vacuum oscillates with a frequency ranging preferably between 1 to 15 Hz, said apparatus allowing the translational movement causes cervix displacement of up to 20 mm in each direction with a frequency of up to 5 Hz, such as up to 2 Hz, and said apparatus supplying vibrations to the cervix with a frequency of up to 300 Hz, such as ranging from 25 up to 300 Hz, said apparatus optionally supplying acoustic waves; and v) extracting uterine and vaginal fluid out of the vagina. These will result in achieving at least one of the following effects: providing the user with predetermined time intervals without menstrual discharge, reducing the overall volume of the monthly menstrual discharge, reducing the duration of menstrual bleeding, reducing menstrual cramps, reducing menstrual pain, and reducing the need for tampons and pads.

The invention is directed toward a system designed for removing uterine and vaginal fluid, comprising a suction cup, connected to a vacuum source, to be inserted into the vagina near the cervix; and a noninvasive cervix-opening means selected from (a) a vacuum regulation means connecting and disconnecting said vacuum source with said cup with a frequency of between 1 and 15 Hz, thereby providing oscillating vacuum to said cup, (b) an apparatus allowing a translational movement of said tube and said cup along said axis in both directions, possibly periodically pulling and pushing the cup away and toward the cervix, (c) an apparatus supplying vibrations to the cervix during the vacuum aspiration, or (d) a combination thereof; the system allows a menstruating woman to plan her activities and avoid inconvenient and embarrassing moments, possibly even without using tampons and pads; it may also provide her with a predetermined time interval without menstrual flow.

The main aim of the invention is lifestyle improvement; however, the device of the invention is useful also in handling and treating menstrual irregularities, including menorrhagia (excessive bleeding) and dysmenorrhea (pains and cramps).

The device, method and system of the invention aim at mitigating inconvenience and discomfort associated with normal menstrual cycle, as well as with menstrual irregularities, while reducing or avoiding the use of tampons, pads, and synthetic hormones for suppressing the menstruation, and enabling a woman in her menstrual period to plan her activities by providing a predetermined time interval free of the menstrual flow.

BRIEF DESCRIPTION OF THE DRAWINGS

The above and other characteristics and advantages of the invention will be more readily apparent through the following examples, and with reference to the appended drawings, wherein:

FIG. 21. shows an example of time synchronization of periodically applied vacuum (bottom) with cervix displacement (top), with the X-axis showing time (relative units) and Y-axis showing the displacement or pressure in relative units; one displacement cycle and several vacuum oscillation cycles are shown (21A); four examples of oscillation waves with sudden high impulse application of vacuum pressure (601) are shown including a square wave, sawtooth wave, and modified sawtooth waves (21B).

DETAILED DESCRIPTION OF THE INVENTION

Figure 1:
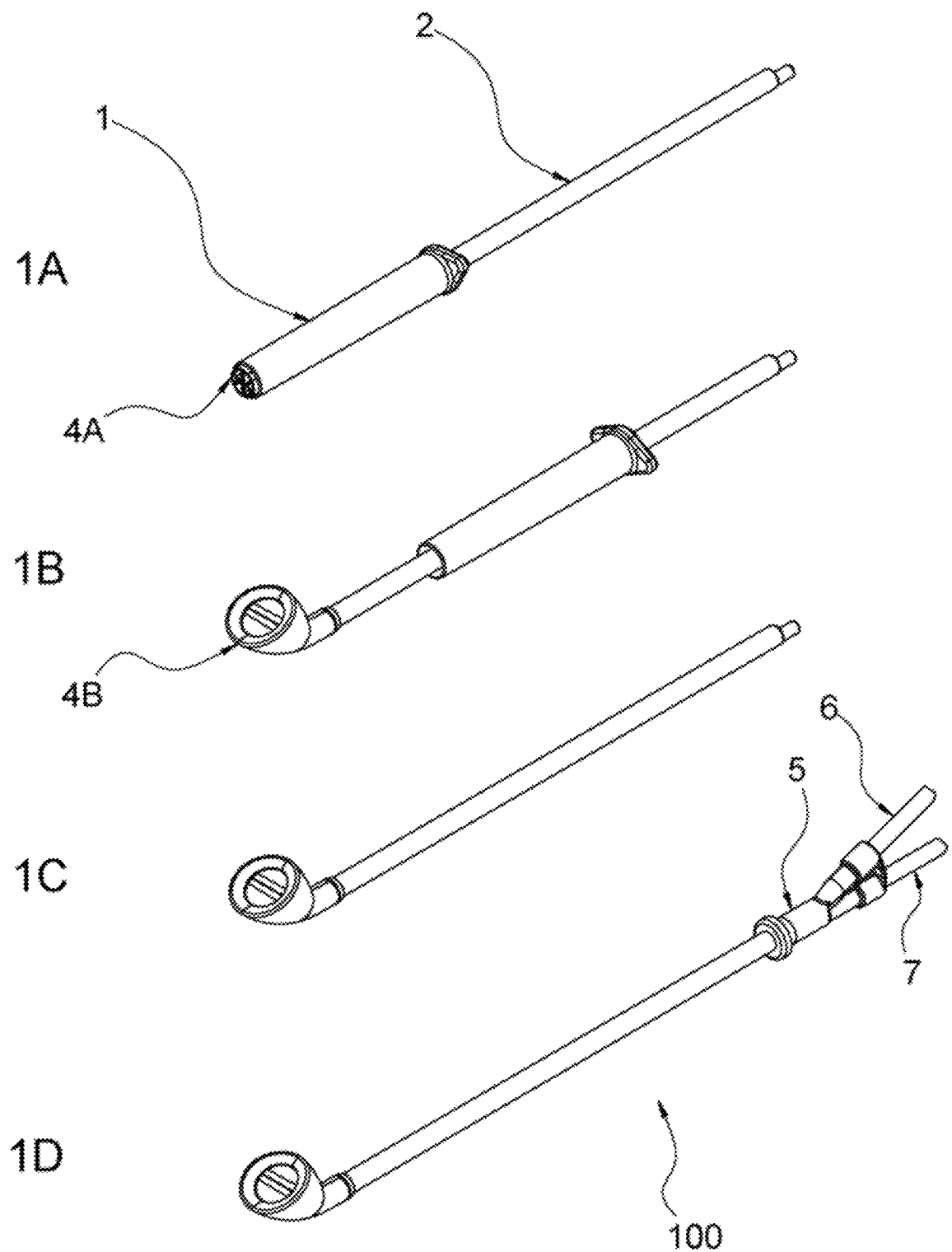
FIG. 1. illustrates a device according to one embodiment of the invention the part of the invention intended to be inserted into the vagina (100, referred to as 'tube-and-applicator assembly' below): 1A) the front part of the semi-flexible tube (2) and the folded cup (4A) are covered with a plastic applicator (1), while the rear part of the tube (2) is exposed (referred to below as 'folded configuration'); 1B) pulling the applicator (1) backwards (away from the body) opens and exposes the cervical cup (4B) (referred to below as 'unfolded configuration'); 1C) the tube and cervical cup are shown without the applicator, which is intended to be removed by the user; 1D) the tube splitter attached by the user to the back end of the tube (5) splits it into two tubes: one connected to the vacuum canister/trap (7) and the other connected to the vacuum-release channel (6).
Figure 2:
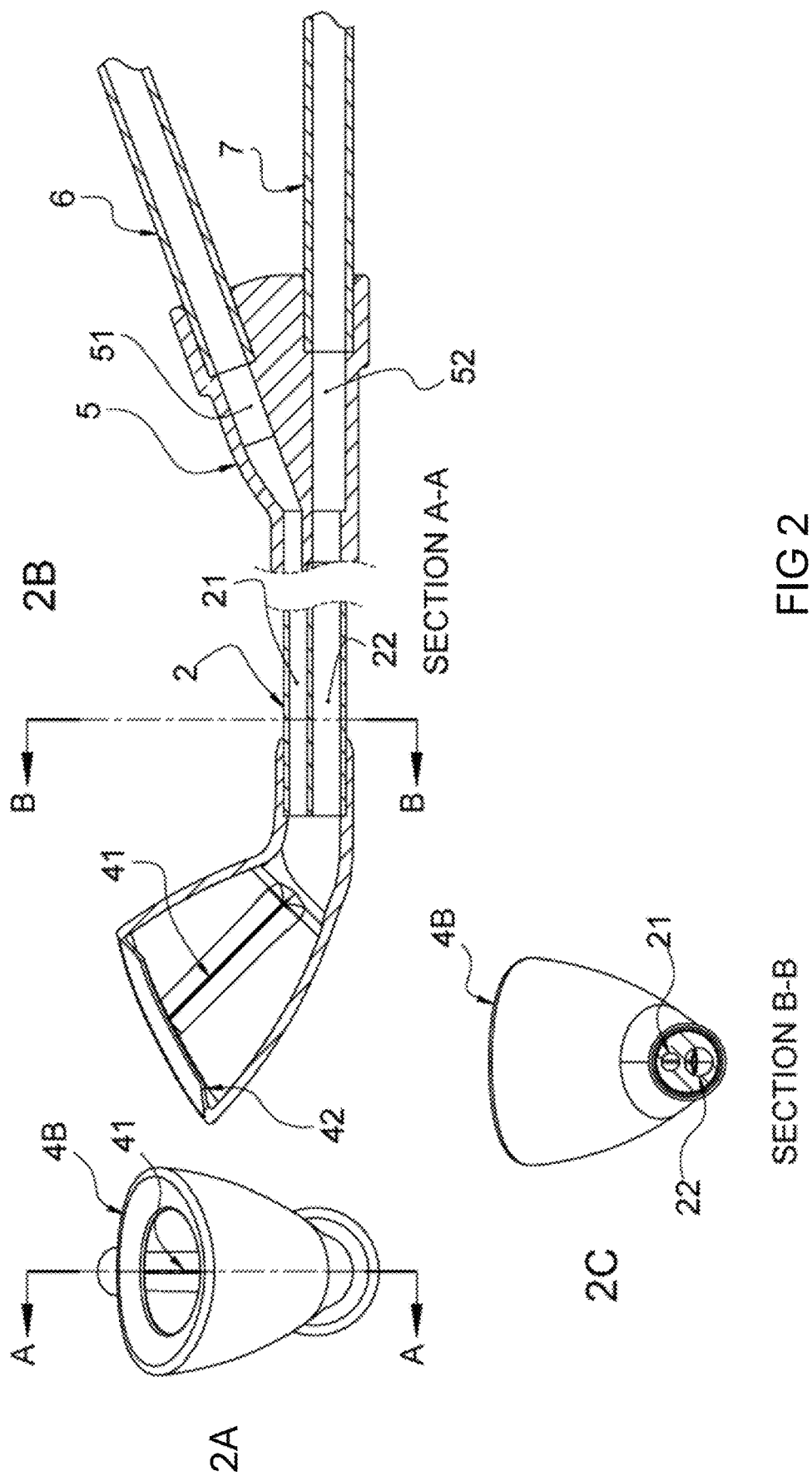
FIG. 2. shows the tube-and-applicator assembly after the applicator was removed (100) with the cup unfolded (4B in FIG. 1) from three views: 2A) front view; 2B) side cross-section view (section A-A), showing the double-lumen tube (2) consisting of a vacuum lumen (22) and a vacuum-release lumen (21), the tube splitter (5) consisting of a vacuum lumen (52) and a vacuum-release lumen (51), and the divergence of the tube into two (6 and 7 as detailed in FIG. 1); also depicted are one of the four splines (41) aimed at keeping the cup fully open and the inner lip designed to seal with the cervix (42); 2C) another section view (section B-B) showing the division of the tube into two lumens (21 and 22).
Figure 3:
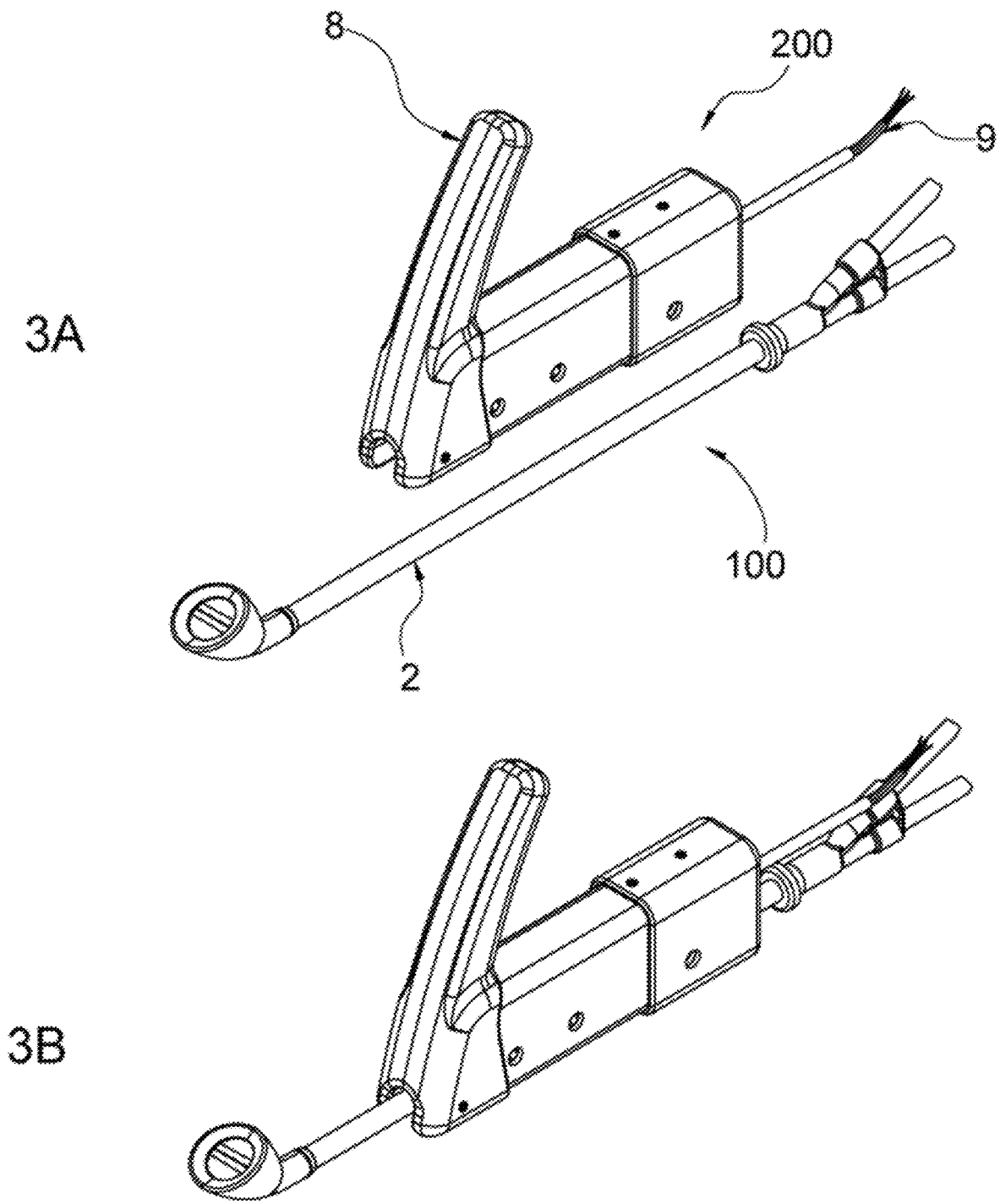
FIG. 3. depicts the tube-and-applicator assembly after the applicator was removed (100 in FIGS. 1C and 1D) along with the motor controlling the pull and push agitations (200), covered by housing, while it is detached (3A) and attached (3B) to the tube (2); also shown are the motor handle designed to allow the user to place the device (8), and the cable connecting the motor to a power source (9).
Figure 4:
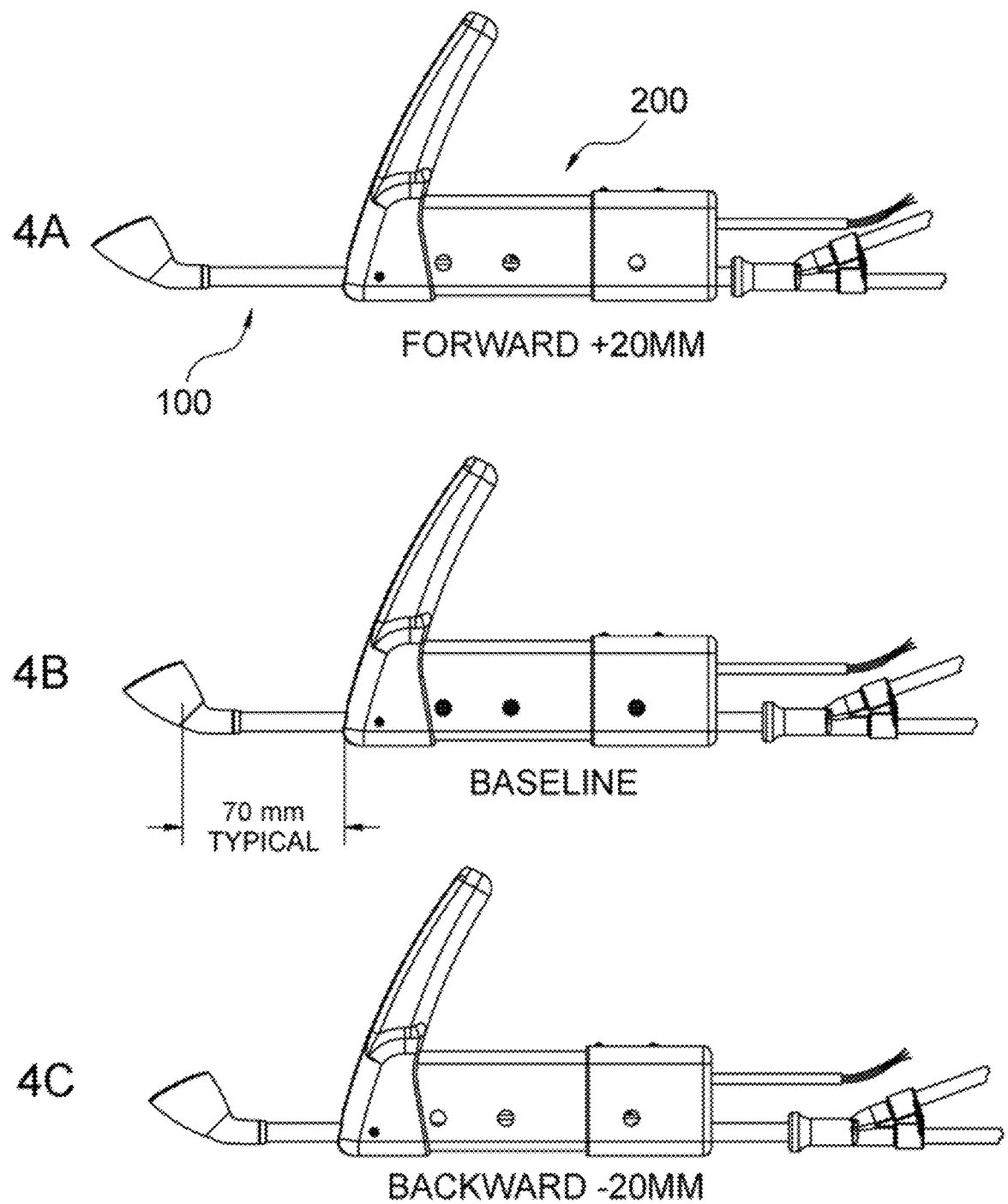
FIG. 4. shows the tube-and-applicator assembly (after the applicator was removed) (100) sliding forward and backward along the motor (200). Three positions are illustrated: 4A) the assembly is at the most forward position (i.e. deepest inside the body), referred to as +20 mm; 4C) the assembly is at the most backward position, referred to as −20 mm; 4B) the assembly is at the baseline position, referred to as 0, where the typical length of the exposed part of the tube (to be inserted into the vagina) is 70 mm (adjustable according to the user's anatomy).
Figure 5:
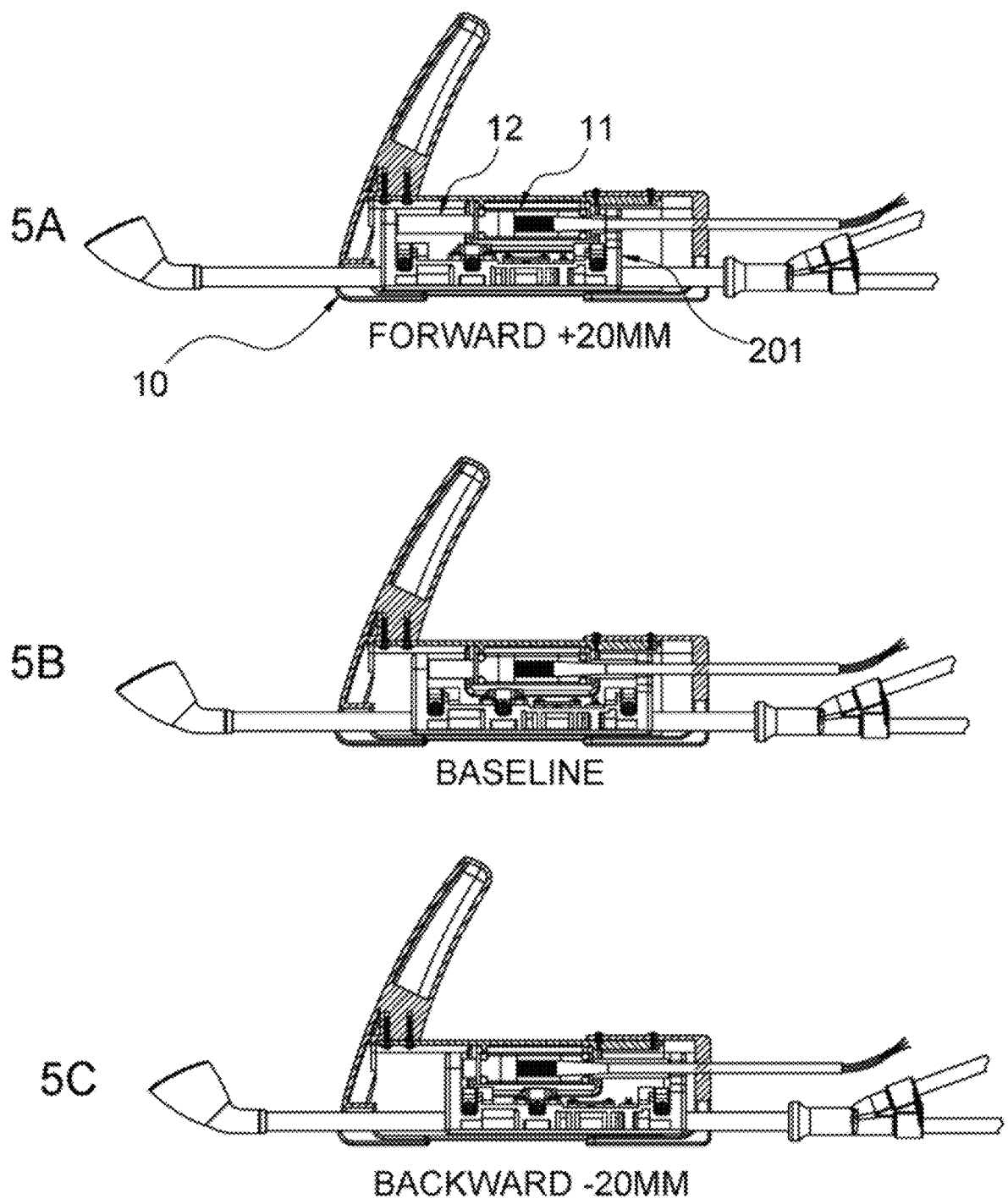
FIG. 5. depicts a motor-housing (10) cutaway version of FIG. 4. The rotor (12) and stator (11) parts of the linear motor, along with the carriage moving back and forth (201), are visible.
Figure 6:
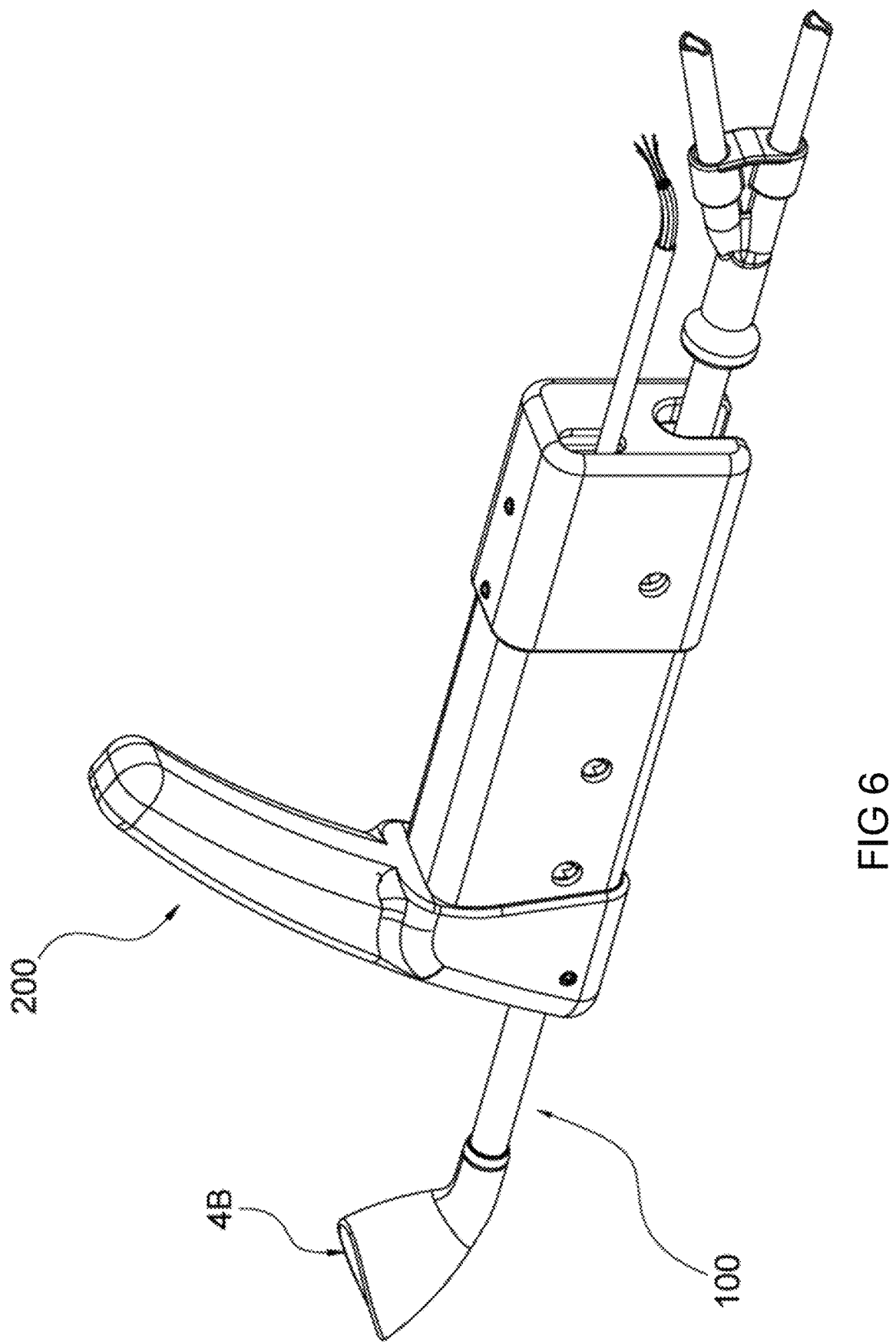
FIG. 6. shows another view of the tube-and-applicator assembly (after the applicator was removed) (100) and the motor controlling the pull and push agitations (covered by housing) (200), while the two are attached to each other.
Figure 7:
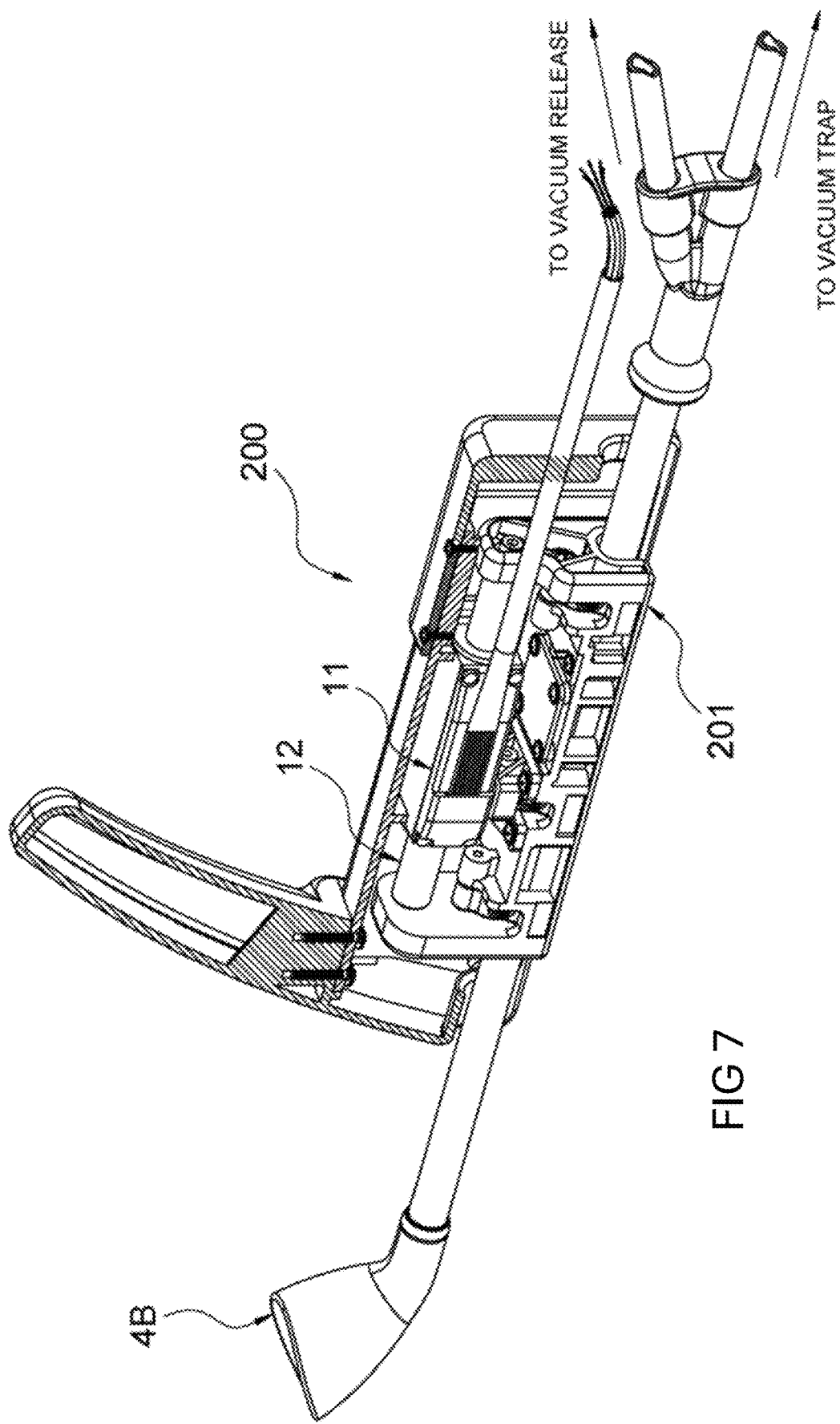
FIG. 7. depicts a motor-housing cutaway version of FIG. 6. The rotor (12) and stator (11) parts of the linear motor, along with the carriage moving back and forth (201), are visible.
Figure 8:
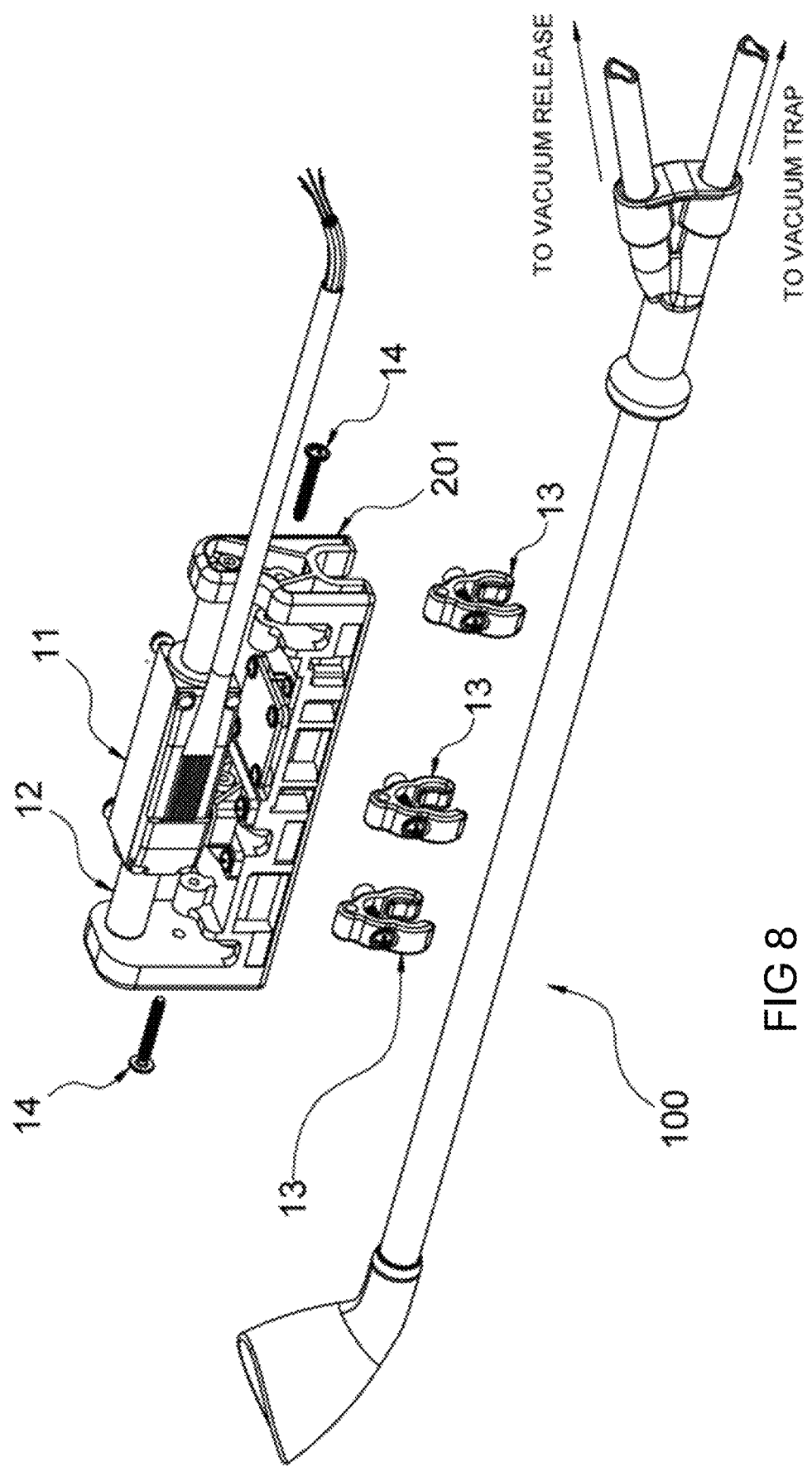
FIG. 8. shows the tube-and-applicator assembly (after the applicator was removed) (100) and motor (200) shown in FIG. 7 without the motor housing and when the parts are detached. The screws (14) and grippers (13) allowing the motor to attach to the tube are shown in exploded views.
Figure 9:
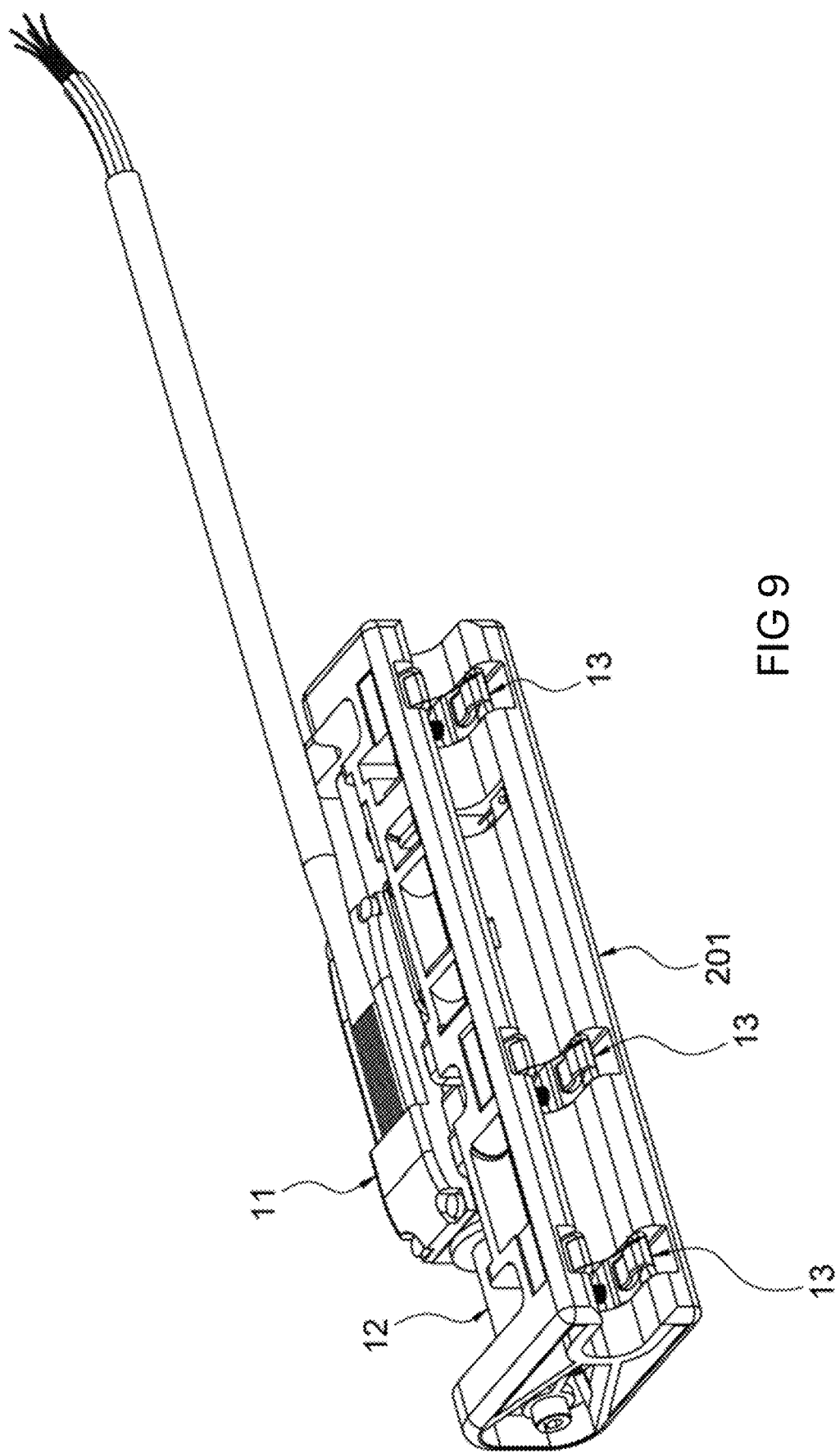
FIG. 9. depicts another view of the carriage (201) assembled with linear motor (11 & 12) and grippers (13).
Figure 10:
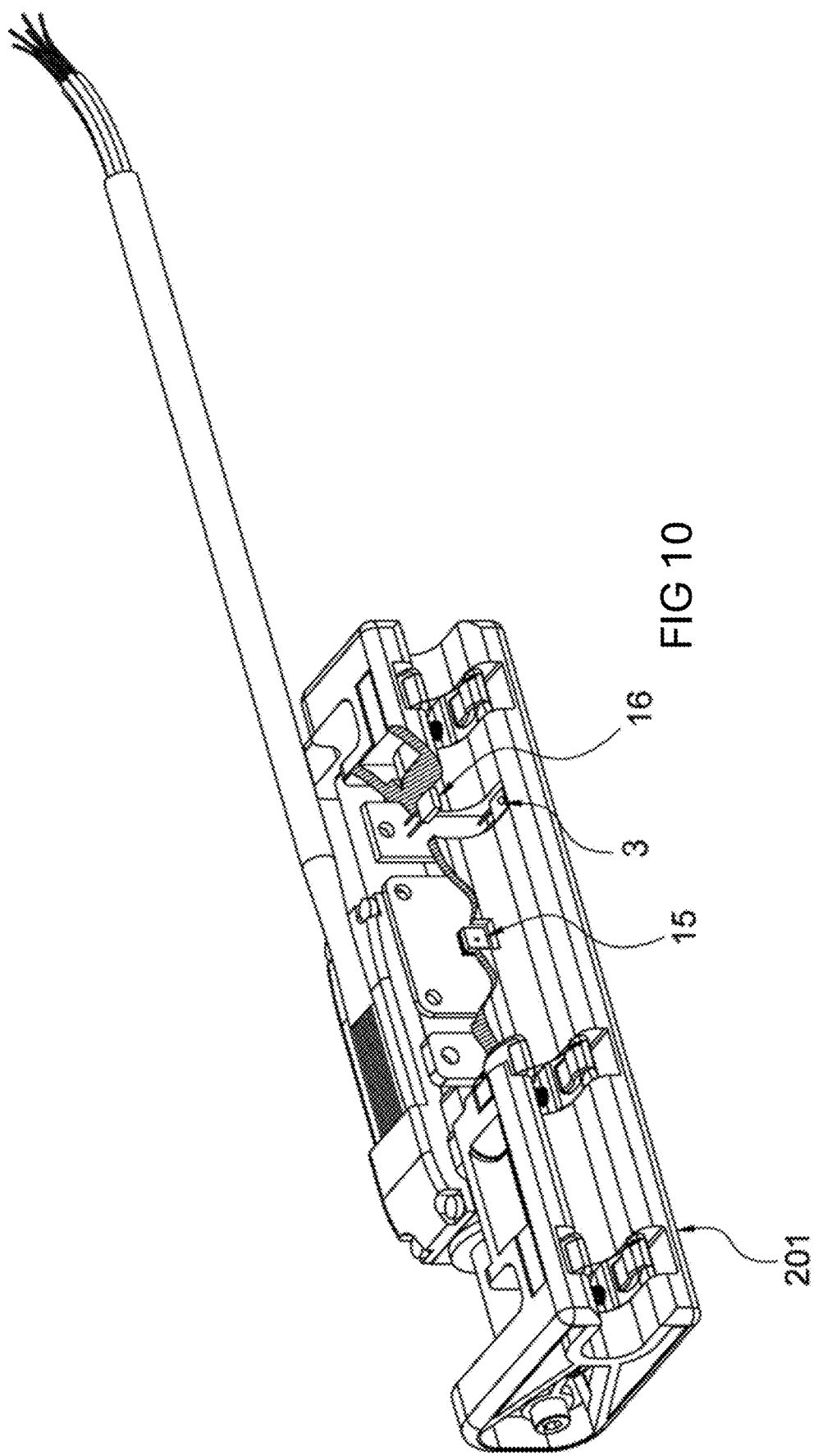
FIG. 10. shows the carriage (201) from the same view as in FIG. 9, with a cutaway exposing a color sensor (15) and an infra-red flow sensor consisting of a sender (16) and a receiver (3).
Figure 11:
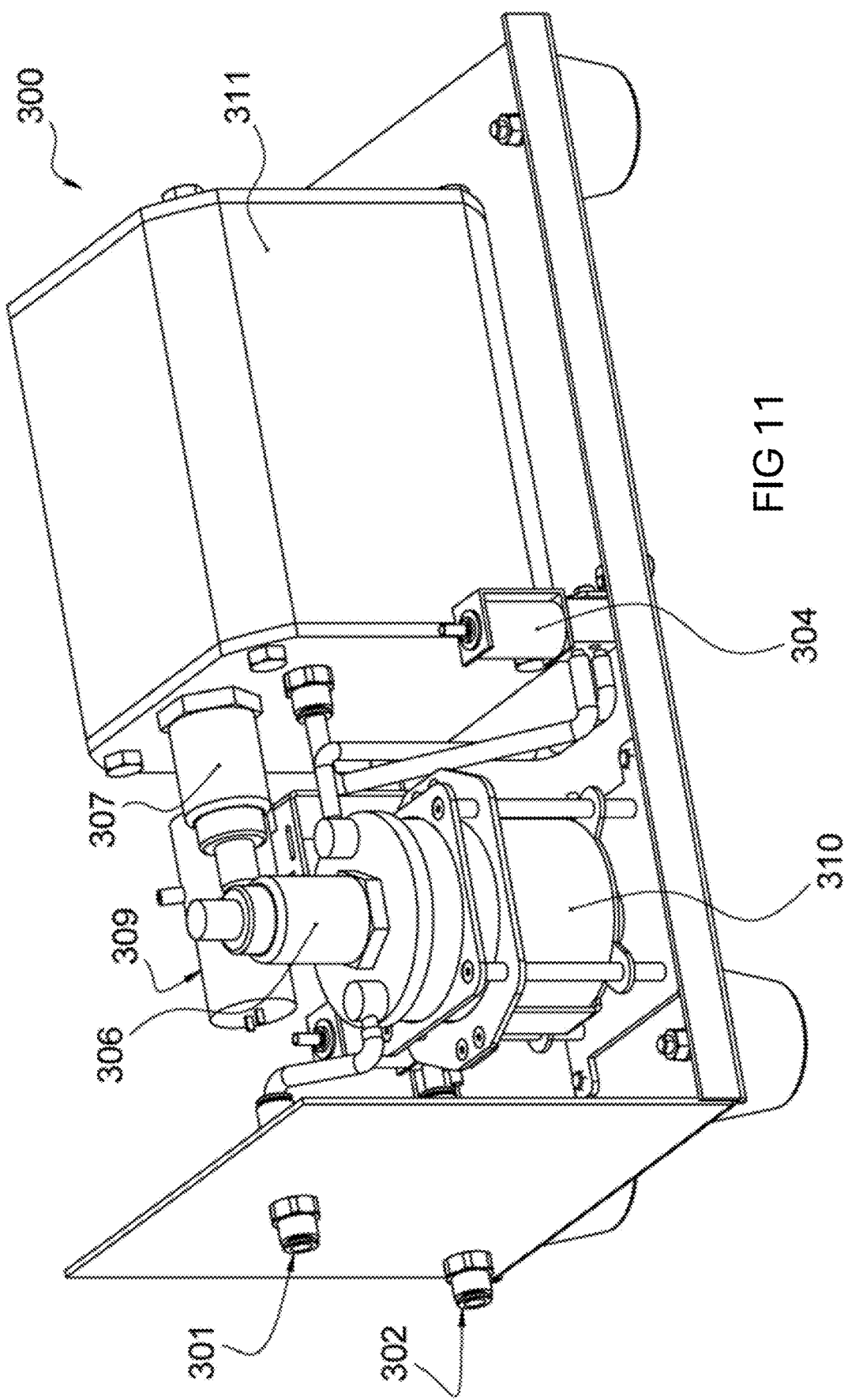
FIG. 11. shows the pump unit (300). The vacuum pump (309), accumulator (311), vacuum valve (304), canister/trap (310), vacuum-tubing connector (301), vacuum-release connector (302), canister pressure sensor (306), and accumulator pressure sensor (307) are visible.
Figure 12:
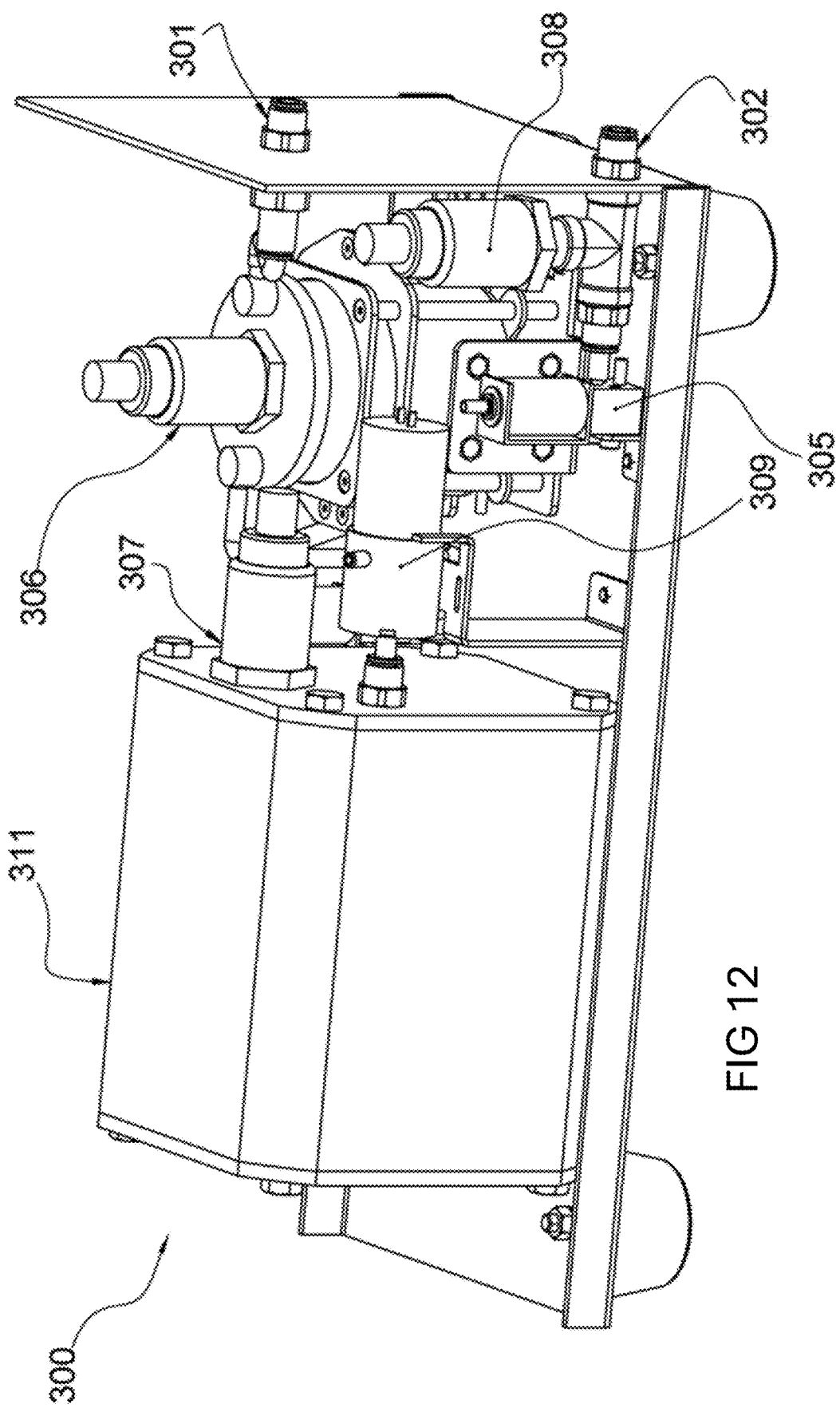
FIG. 12. depicts another view of the pump unit (300) shown in FIG. 11. The vacuum pump (309), accumulator (311), release valve (305), vacuum-tubing connector (301), vacuum-release connector (302), canister pressure sensor (306), accumulator pressure sensor (307) and vacuum-release pressure sensor (308) are visible.
Figure 13:
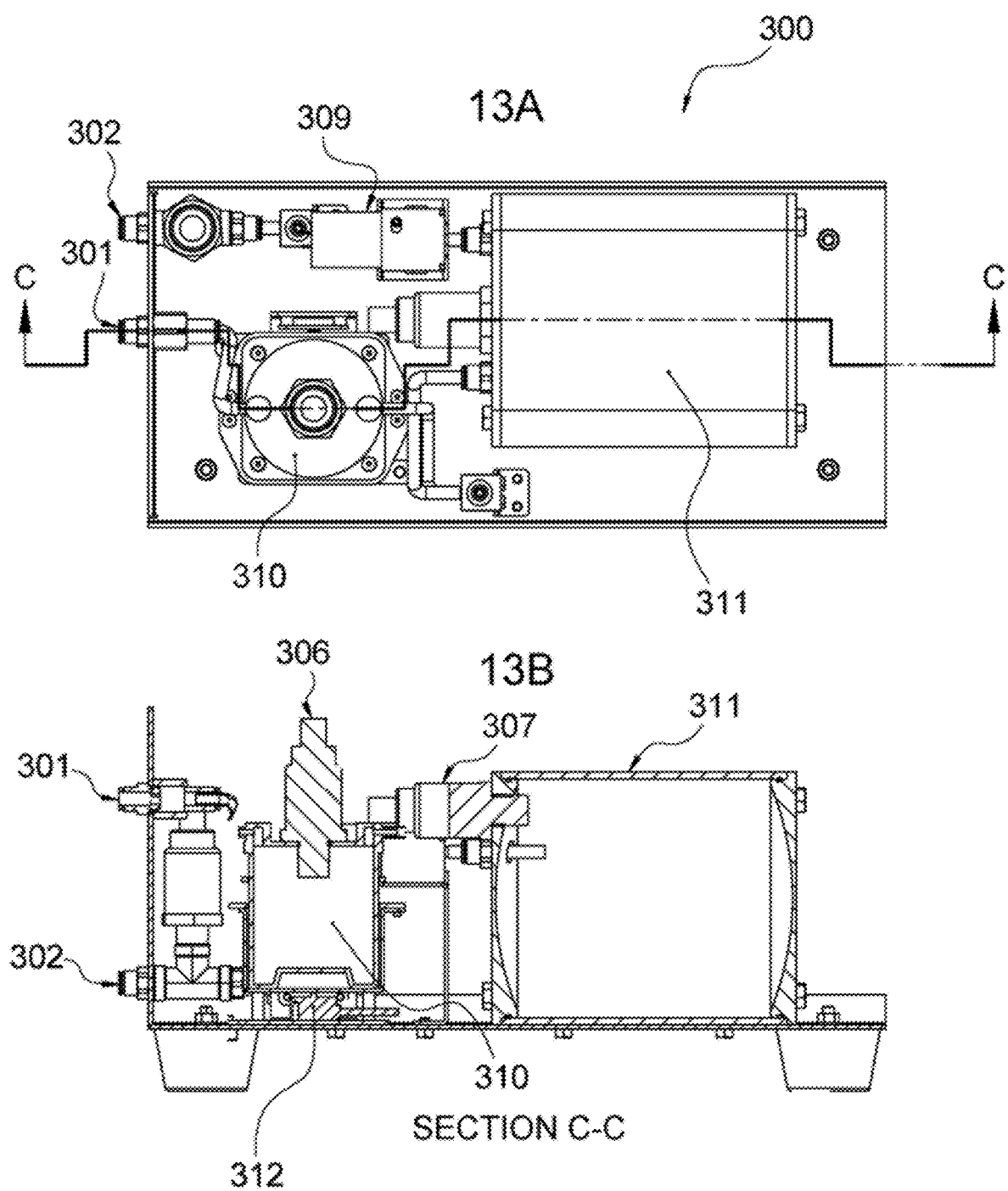
FIG. 13. shows another views of the pump unit (300): 13A) top view, where the vacuum pump (309), accumulator (311), canister/trap (310), vacuum-tubing connector (301) and vacuum-release connector (302) are visible; 13B) a side section view (section C-C), where the canister/trap (310), accumulator (311), vacuum-tubing connector (301), vacuum-release connector (302), canister pressure sensor (306), accumulator pressure sensor (307), and load cell (312) used to measure the mass of the canister/trap, are visible.
Figure 14:
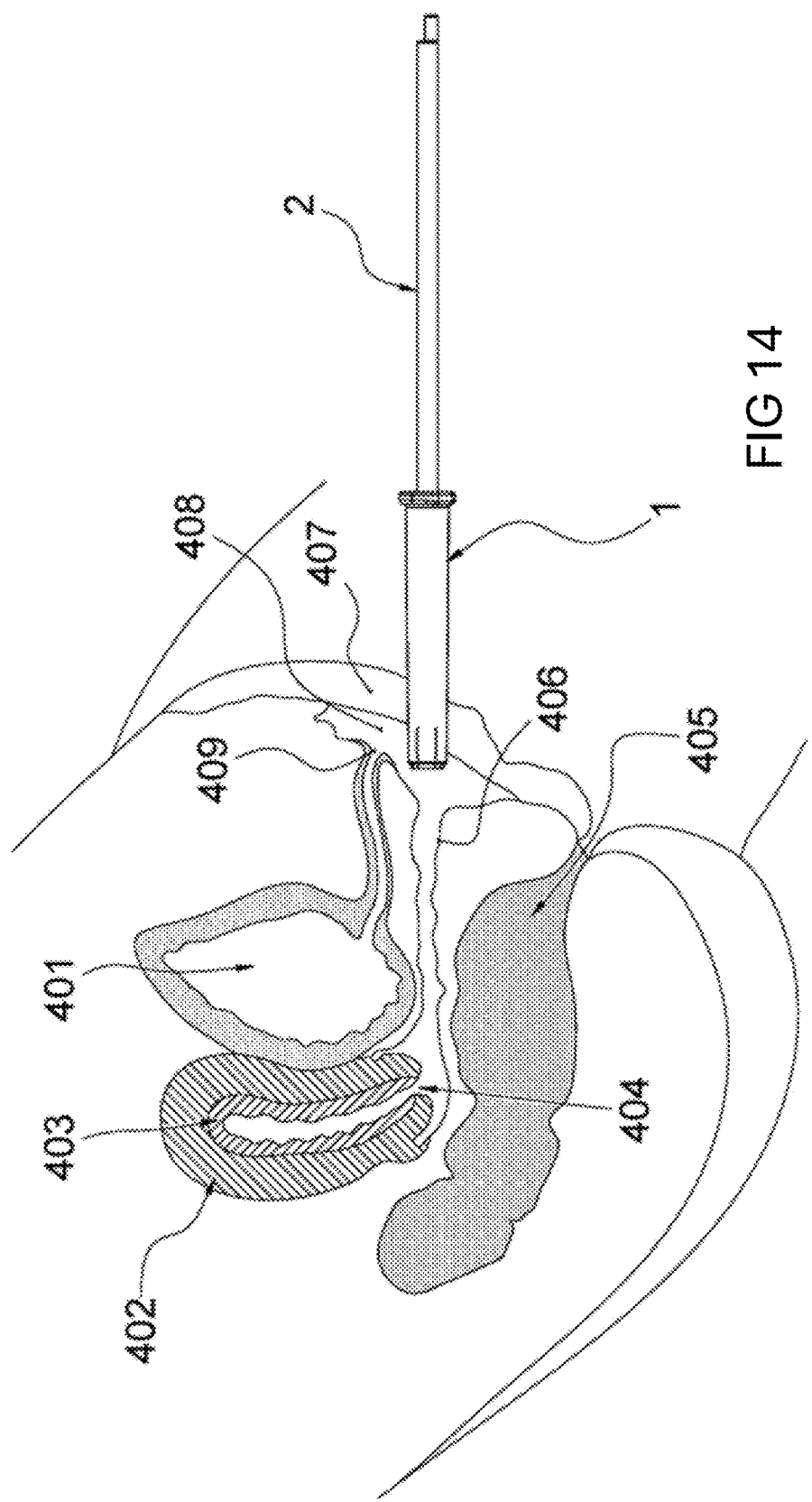
FIG. 14. shows a cross-sectional view of the female body, where the rectum (405), bladder (401), vagina (406), urethra (409) labia minora (408), labia majora (407), and uterus—including the myometrium (402), endometrium (403) and cervix (404)—are visible. The tube (2) and applicator (1) (of the part of the device intended to be inserted into the vagina (100) in a folded configuration, FIG. 1A) are shown while located outside the body.
Figure 15:
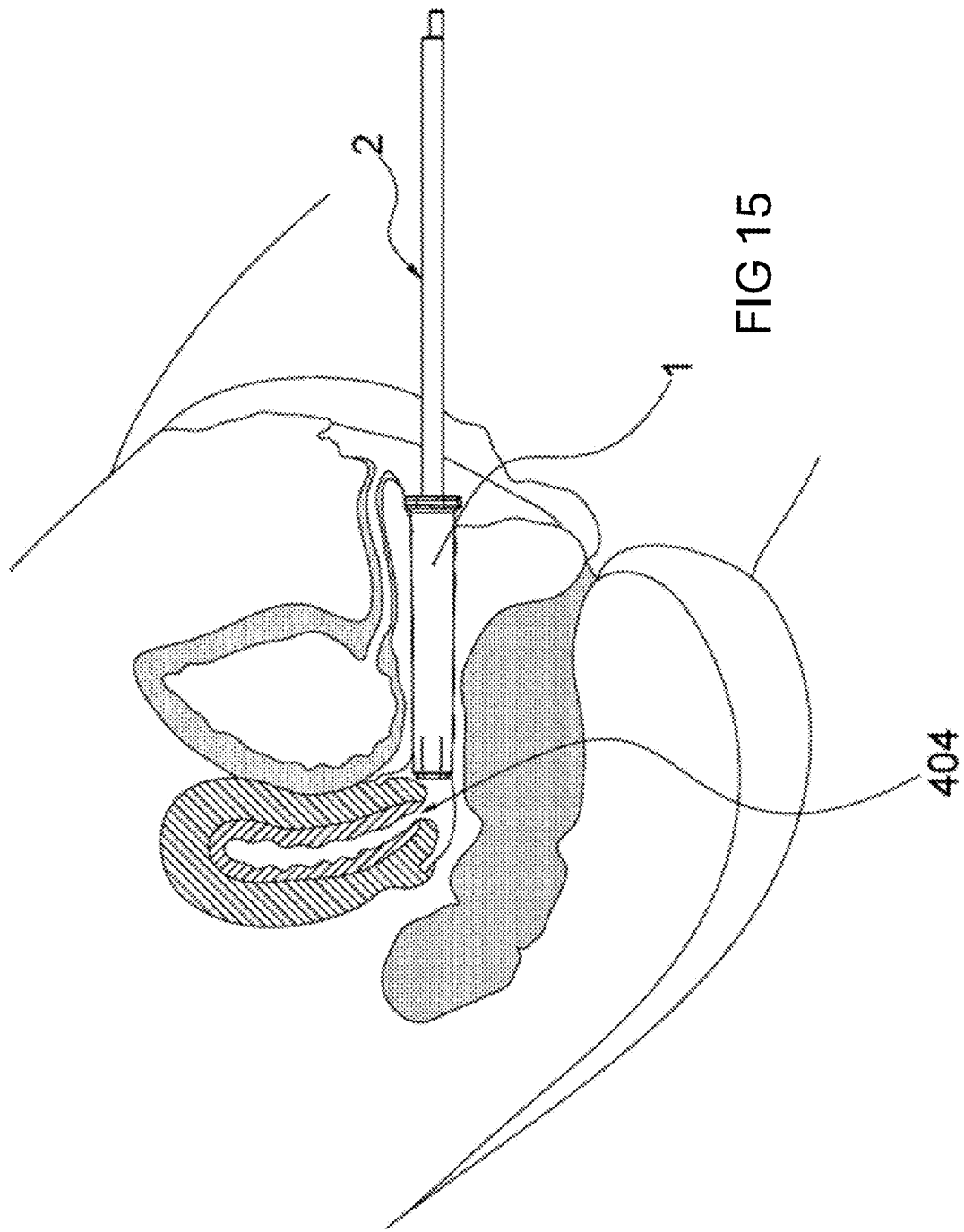
FIG. 15. depicts the cross-sectional view of the female body shown in FIG. 14, with the tube-and-applicator assembly in a folded configuration (FIG. 1A) inserted into the vagina and approaching the cervix (404).
Figure 16:
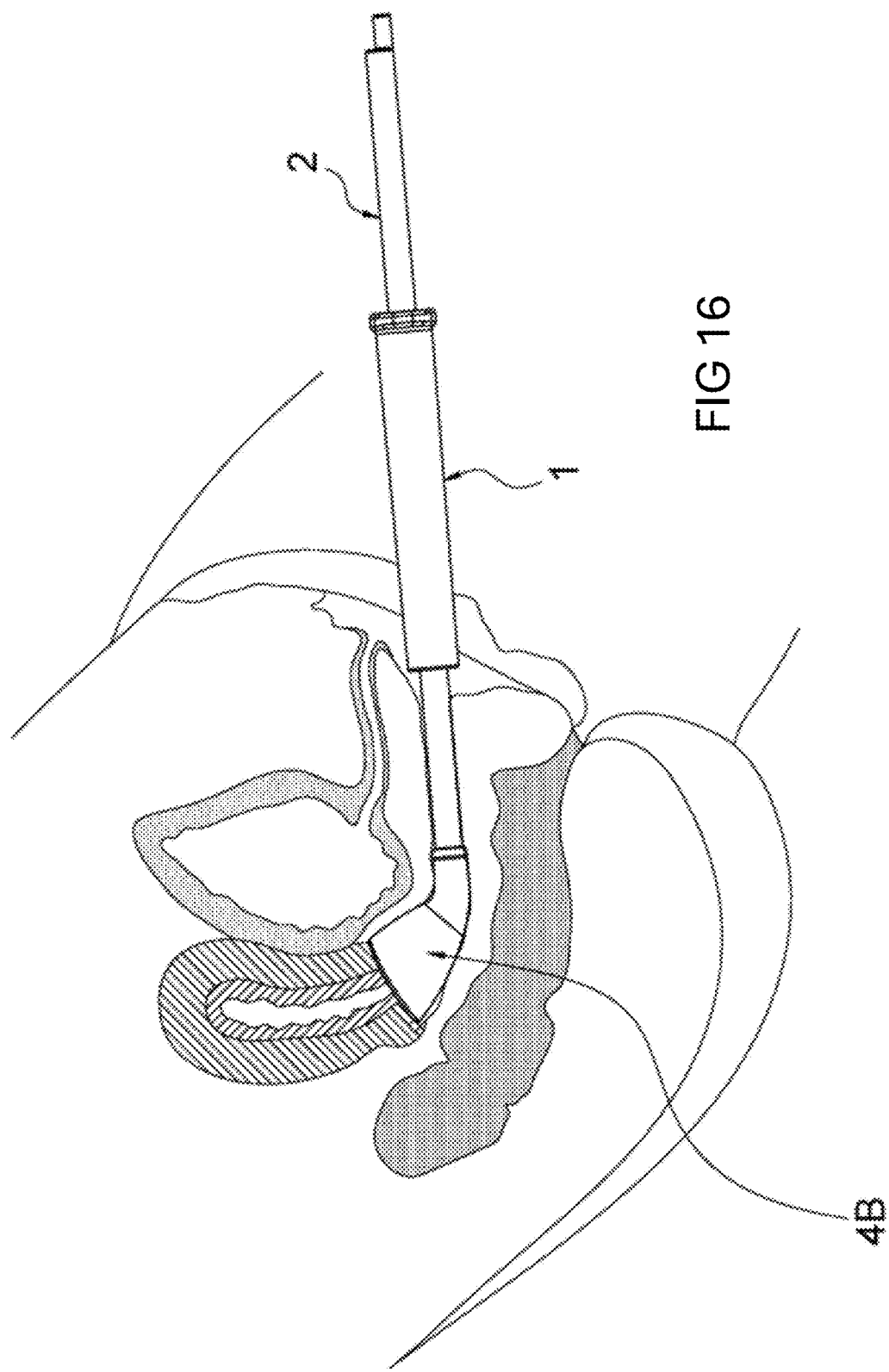
FIG. 16. shows the tube-and-applicator assembly approaching the cervix after the applicator (1) was pulled backward along the tube (2), thereby exposing and opening the cup (4B) as illustrated in FIG. 1B (unfolded configuration). The cup docks and seals with the cervix (404).
Figure 17:
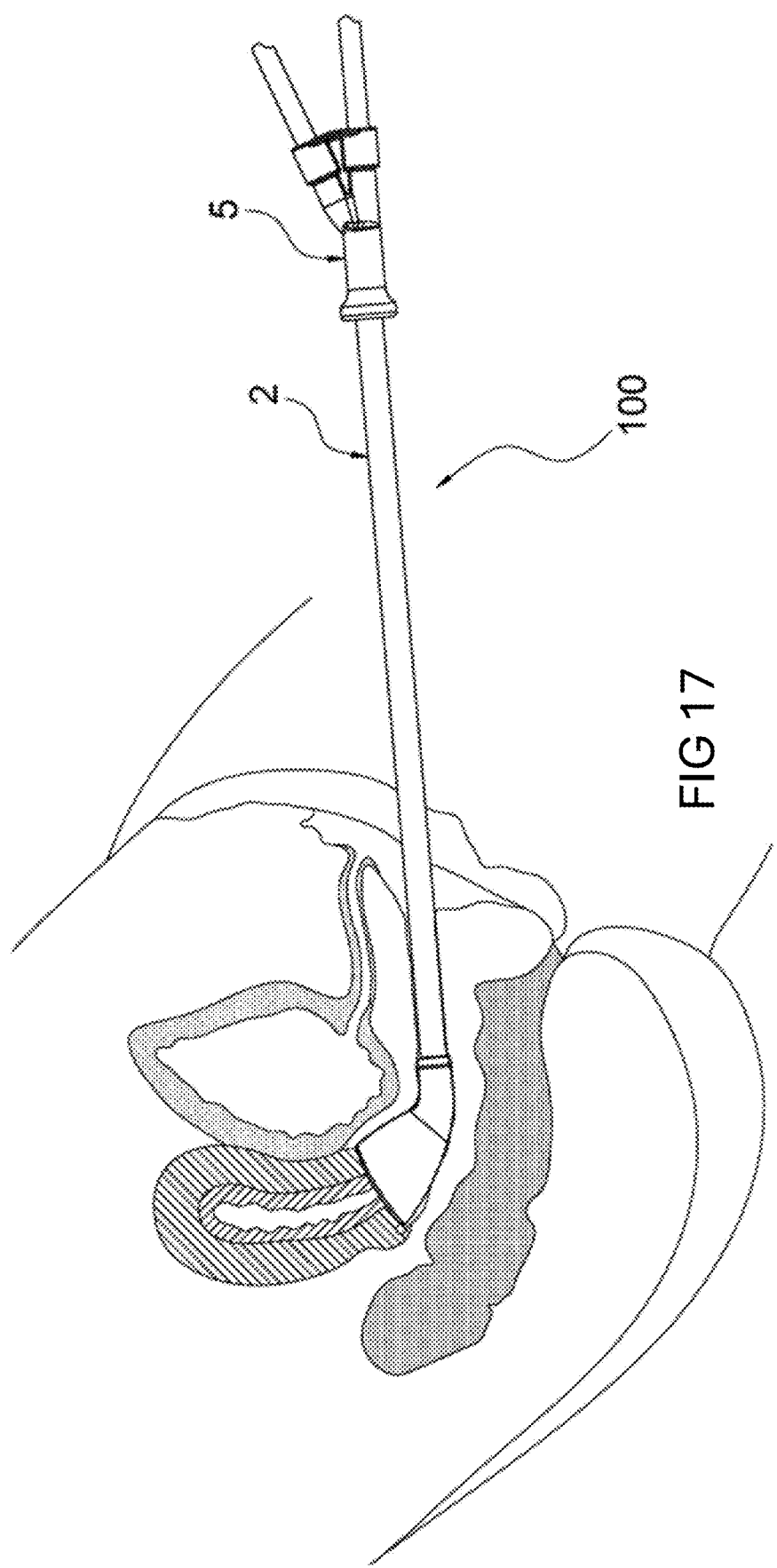
FIG. 17. depicts the tube-and-applicator assembly (100) with the cup docking with the cervix (as in FIG. 16), after the applicator (1) was removed (as in FIG. 1D). The tube splitter (5) is now attached to the tube (2).
Figure 18:
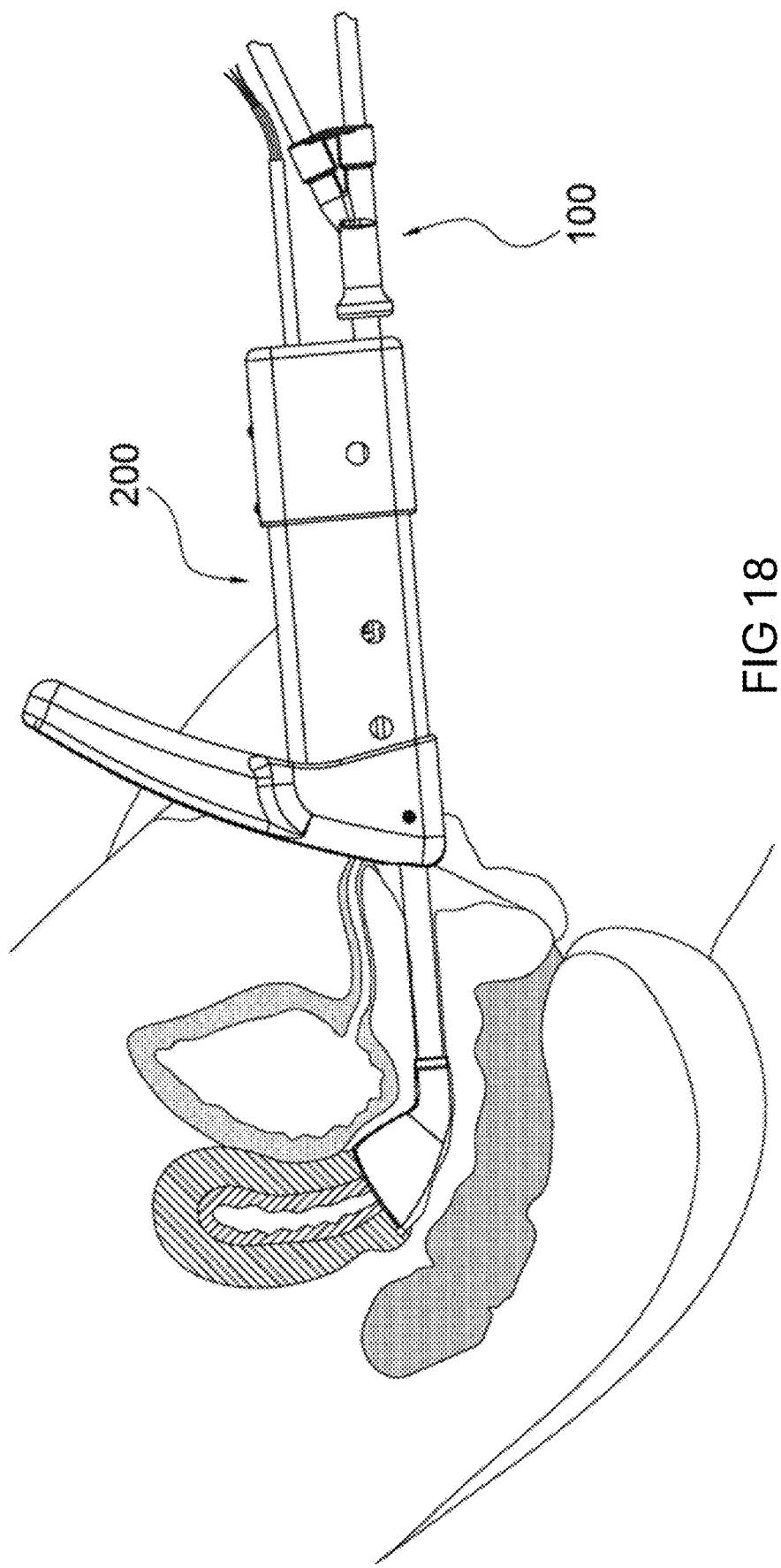
FIG. 18. shows the tube-and-applicator assembly (100) with the applicator removed and the cup docking with the cervix (as in FIG. 17), along with the motor controlling the pull and push agitations (200), covered by housing, attached to the tube (as in FIG. 3B).
Figure 19:
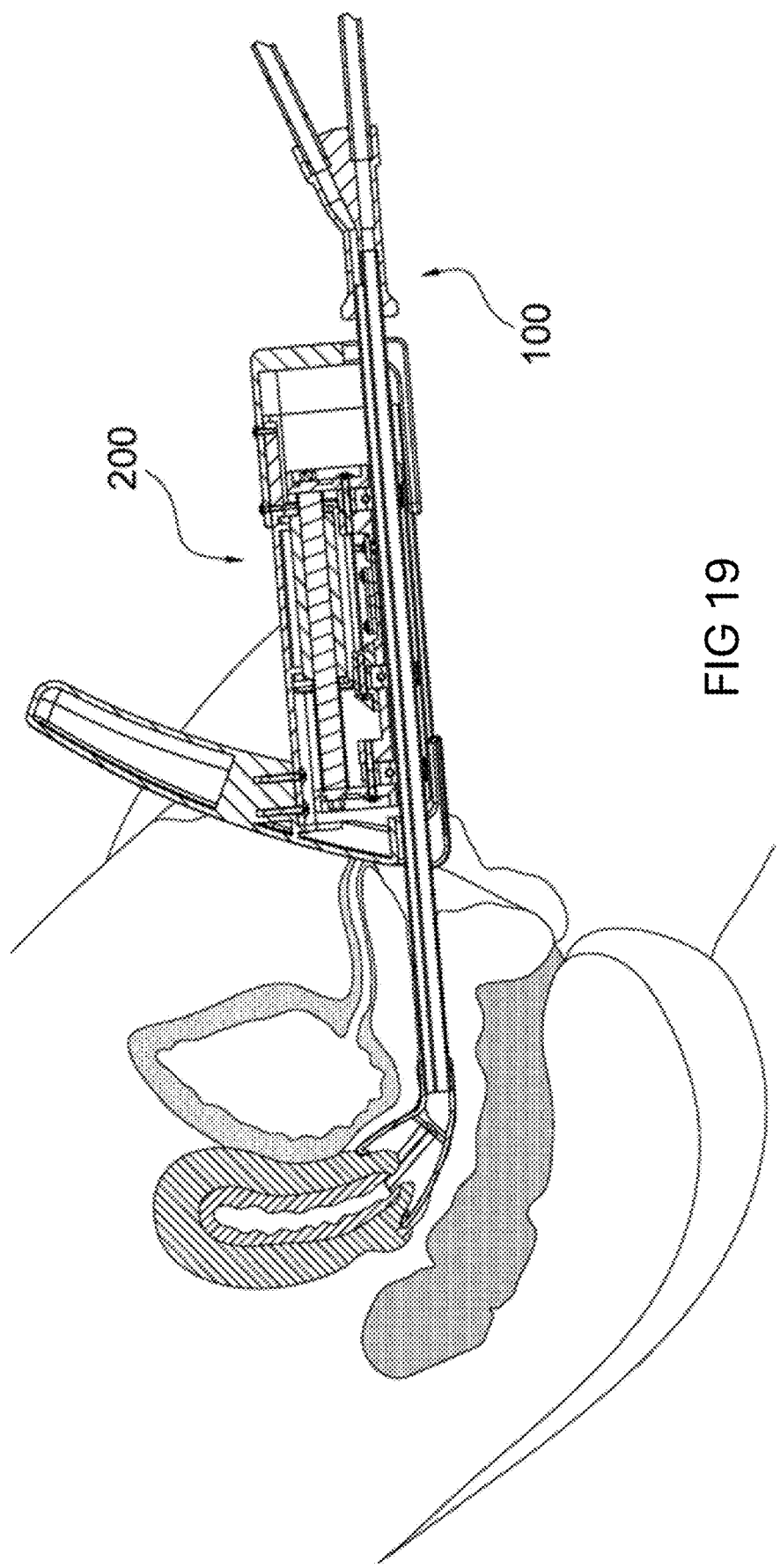
FIG. 19. depicts the tube-and-applicator assembly (100) and motor covered by housing (200) shown in FIG. 18 in a cutaway version.

It has now been found that menstrual fluid can be efficiently removed from the vagina and uterus in order to reduce the duration of menstrual bleeding and to secure a flow-free time interval, comprising aspirating the vaginal fluid while simultaneously applying periodic vacuum oscillations and cervix displacements.

In one embodiment of the system according to the invention, fluid is drawn from uterus by a device of which aspirating ending cup may dock to the cervix. The device removes menses mainly from the uterus, but it may draw liquid also from outside the uterus and inside the vagina, especially when the motor retracts the cup away from the cervix. The menstrual extraction device consists of a vacuum pump, a vacuum accumulator, two high-speed switching valves for exposing the cervix to alternating atmospheric pressure and vacuum pressure, a canister (trap) for collecting the menses, tubing, a linear motor enclosed in a protective case which also acts as a locating surface against the vagina, a stiff yet flexible dual lumen tubing, an asymmetrical cup attached to the stiff flexible tubing which docks with the cervix and moves in an axial direction, pushing against the fornix of the cervix and pulling away from the cervix. The device may also have several sensors including pressure sensors on the accumulator, canister, and the cup. The device, particularly during laboratory testing but also in real use, may have an IR sensor for indicating the flow of menstrual fluid, a scale for weighing the canister, and a spectral sensor for analyzing the color of the extracted menses.

The menstrual extraction according to the invention has at least one of the following effects: providing the user with predetermined time intervals without menstrual discharge, reducing the overall volume of the monthly menstrual discharge, reducing the duration of menstrual bleeding, reducing menstrual cramps, reducing menstrual pain, and reducing the need for tampons and pads.

More generally, the invention aims at efficiently removing menstrual fluid from the vagina and uterus in order to reduce the duration of menstrual bleeding and to secure a flow-free time interval, comprising aspirating the vaginal and uterine fluid while simultaneously applying periodic vacuum oscillations while precluding the collapse of the cervix (closure) by employing cervix opening means. Typically, during menstruation there is positive pressure (~50 mbar) inside the uterus and atmospheric pressure outside the vagina; this causes a slow flow of menses through the cervix, which keeps it from collapsing. The cervical tissue itself has some structural strength which keeps it open. The cervix itself extends into the vagina in such a way so that when the vacuum pressure outside the cervix is above a certain threshold, the passageway may collapse; increased vacuum pressure and the absence of fluid passing through the canal may cause narrowing or complete closure of the canal. Without wishing to be limited by any particular theory, the inventors believe that the mechanism may comprise physical spreading of the collapsed cervical walls apart with agitation, or it may comprise increasing the intra-uterine pressure, which forces the cervix to open. The cervical canal through which menses are drained during menstruation may intermittently close (by a mechanism of collapse/pinching) when applying vacuum pressure to the external cervical os. The inventors assume that closing depends on the magnitude and frequency of pressure applied, as well as the cervical anatomy and the mechanical properties of the cervical tissue. Closing may be the outcome of three independent mechanisms: a) the cervical canal is not necessarily open when relaxed (i.e., when no external forces are applied), but is likely to be intermittently pinched; this is visible in MRI and US images of the uterus; b) applying vacuum pressure to the cervical lips pulls them away from the uterine corpus, thereby causing the cervix to stretch; this results in axial (i.e., along the axis of the cervical canal) elongation and transverse (i.e., in the plane perpendicular to the cervical canal) narrowing of the cervix, which translates into narrowing of the cervical canal; c) applying vacuum pressure to the cervical canal while no fluid (or not enough fluid) passes through (e.g. due to a block occurring in the vicinity of the internal cervical os) translates into increased pressure being exerted to the walls of the cervical canal (according to Bernoulli's principle). Such increased pressure and the absence of fluid passing through the canal causes narrowing and finally complete closure of the canal through collapse/pinching.

The device according to the invention is particularly effective due to applying vacuum in such a way that the cervix does not collapse. In a preferred embodiment mechanical displacements of the cervix are employed together with vacuum oscillations, in another embodiment high frequency and high amplitude vacuum oscillations are employed. For example, by applying high amplitude vacuum very quickly wherein the oscillation has the form of a square wave or a sawtooth wave, with fast vacuum increase and slow vacuum release, aspiration is achieved prior to eventual collapse of the cervix. If the vacuum is applied over longer periods of time and its strength is gradually increased, the cervix may collapse, and a further increase in suction pressure may be ineffective. A preferred way to prevent the cervical collapse is creating agitation of the cervix by said mechanical displacement, for example by pushing and pulling it with the suction cup. Another way includes applying vibrations to the cervix during vacuum aspiration. The vibration may encourage a collapsed cervix to open, or prevent the cervix from easily collapsing. The vibration may also stiffen the viscoelastic tissue of the cervix preventing its collapse, or change the viscosity of the uterine fluid so to encourage flow.

Thus, in a preferred embodiment, the invention provides a device comprising at least a vacuum pump, a suction tube with a suction cup, a liquid trap, a processor, and a cervix opening means which apply vacuum pressure and prevent cervix collapse. Said means may prevent the cervix from collapsing by applying the vacuum pressure very quickly (high impact or high frequency), by applying axial force to the cervix (push, pull), and/or by applying vibration to the cervix. The device of the invention preferably comprises at least one of the options selected from square wave or sawtooth pressure oscillations, translational axial movement/force, and vibrations; in one embodiment, the device includes at least two of said options. In one embodiment, the device may employ acoustic waves.

One of the important features of the device and method according to the invention is their noninvasive character; the cervical canal is not crossed, and the structure of the device precludes such crossing or entering the cervical canal.

The invention thus provides a system including vacuum-regulation means which comprise pressure oscillations, preferably with a quick pressure start, such as from 0 to −700 mbar, for example comprising square tooth waves, together with cervix displacements of up to 20 mm to both directions, and/or together with mechanical vibrations. The vacuum oscillations may have a frequency of from 1 to 25 Hz, such as 1 to 15 Hz, such as between 2 to 15 Hz, for example 4 and 15 Hz. The linear displacement may have a frequency of 1 to 6 Hz, such as from 2 to 5 Hz. The mechanical vibrations applied to the cervix may have a frequency of 25 to 300 Hz, such as from 40 to 100 Hz. The vibrations may have a non-zero axial and a non-zero transverse components. Acoustic vibrations may be employed, comprising either sound or ultrasound, using the energy outputs known from massage devices used on the human body.

One of the most important features of the system and the device according to the invention is a simultaneous application of the following activities: (a) a mechanical translational movement of up to 20 mm forward and 20 mm backward from a docking baseline, and (b) pulses of vacuum pressure exhibiting pressure values between approximately 0 to −600 mbar gauge pressure at a frequency of up to 15 Hz. In a preferred embodiment of the invention, the translational displacement is synchronized with the pressure pulses. Additional features of the invention include a color sensor which continuously monitors the color of the menses, thereby providing an indication for the progress of extraction and the health state of the user.

Another aspect of the invention includes a flow sensor. It allows the system, together with the controller, to "learn" the user and modify the critical parameters of the device, including vacuum-pressure amplitude, vacuum-pressure frequency, forward and backward displacement, displacement frequency, and synchronization between vacuum oscillations and displacement oscillations. It can further adapt intervals as part of a personalized regimen optimized to the patient. Specific parameters characterizing a user can be obtained, before employing the device, from an expert or doctor, including a gynecologist, or via a questionnaire filled in by the user; the parameters include surgical history, vaginal deliveries and caesarean sections, fibroids, further relevant history and other information which may affect the optimal regimen.

Another feature of the system according to the invention is optionally incorporating a priming phase into the regimen before the main extraction phase; the priming phase may include, for example, a lower frequency or a weaker vacuum than the main phase. The structure of the phases is adapted to the user.

In one embodiment of the invention, a fluid aspirating device comprising a suction tube with an ending cup configured to independently apply vacuum pulses and to move along its axis forward and backward, removes uterine and vaginal fluid by simultaneously applying pressure pulses and mechanical displacements according to a predetermined regimen. Said pulses of vacuum and/or air pressure preferably result in vibrations in the adjacent tissues, including cervix, and facilitate the flow of the said fluids. Said regimen may, in some embodiments, include cleansing cycle during or after liquid extraction, and a vibration mechanism for pain relief.

The invention is directed to a device and a system for removing uterine fluid comprising blood, water, electrolytes, mucus, plasma, cells and tissue shreds, wherein the fluid is extracted and aspirated via a vacuum source out of the vagina. Said uterine fluid may comprise clots of coagulated blood. The system and the device comprise at least: i) a vacuum pump or other source; ii) a suction tube having a first and a second end, connected with said pump via said first end, at least a part of the tube defining a linear axis; iii) a suction cup connected with said tube via said second end and being wider than said tube, the cup usually comprising a smaller opening attached to the tube and a wider opening for aspirating said fluid; iv) a vacuum valve or analogical instrument for alternatingly connecting and disconnecting said pump with said cup, or for providing oscillating vacuum, with a frequency of between 1 and 15 Hz; wherein the amplitude of the gauge pressure may be between −150 and −800 mbar (corresponding to 150 and 800 mbar underpressure), such as between −300 and −700 mbar gauge, for example between −400 and −600 mbar gauge; and the actual pressure differences between the minimal and maximal negative pressures within one oscillation period may be between 5 and 600 mbar, for example between 30 and 300 mbar; v) an apparatus allowing a translational movement of said tube and said cup along said axis in both directions of up to 40 mm, usually comprising movement from the initial position by 5-20 mm in each direction; the apparatus usually comprising an engine and an attachment member for connecting said suction tube with said engine; vi) one or more pressure sensors, for example for measuring the pressure after the pump or in the collection container (canister/trap), before the cup, or at some other points of the device; vii) a liquid trap connected between said pump and said suction tube for holding said fluid, preferably made of a well washable or disposable plastic; and viii) data logger or microprocessor receiving data from said sensors, controlling the performance of said pump, said valve or other vacuum-regulation means, and said engine, and storing software determining the device working regimen. In a preferred embodiment, the system and the device according to the invention comprise means for cutting said blood clots or tissue shreds to smaller pieces preferably before entering said suction tube; in some embodiments, the means comprises a rotating cutting member or a network of cutting thin wires, wherein said sucked uterine fluid moves through said rotating member or said network of wires, larger clods or clots thus being divided to smaller pieces. Said rotating member may comprise a rotating disc with a shutter provided with a cutting edge. Said network of wires may comprise a strong flexible metal or polymer material.

Said rotating disc with a leading fine edge can cut up, mix, and homogenize the menses and ensure that it passes through the rest of the passageways easily. The disk may rotate approximately 1-10 times per second. The disk may also control the valve pulses. In a preferred embodiment, said suction cup and said suction tube are disposable. Baseline pressure inside a human uterus during menstruation can be approximately 50 mbar between contractions. So in order to equalize this pressure and allow the cervix to experience equal pressure on either side it may be necessary to use small positive pressures. In one embodiment of the invention, the application of negative pressure may be followed by the application of a lower positive pressure, such as up to between 10 and 200 mbar, for example between 40 and 150 mbar. In another preferred embodiment, said cup and said tube form a single integrated disposable plastic unit. Said cup is made of a medical-grade plastic and comprises a surface being convex on the side of said suction tube. The cup and the tube are smooth, without any sharp or irritating elements. The suction tube and the cup are configured to be inserted into the human vagina and to adhere to the cervix, while aspirating said fluid. Said translational movement usually results in moving said cup up to approximately 10 mm or up to approximately 20 mm, such as up to 15 mm in each direction, which results in displacement of said cervix by similar distances. In some embodiments, said pump provides a maximal vacuum pressure (suction pressure or underpressure) of between −200 and −800 mbar gauge, said valve produces pressure oscillations of a frequency of between 4 and 10 Hz, while said cervix displacement is up to 15 mm. The working parameters may be adjustable by the user, and they may be optimizable by the device, possibly in accordance with experts' advice.

The invention is directed to a device for use in managing menses via removing uterine fluid during menstruation, resulting in at least one of the following effects: providing the user with predetermined time intervals without menstrual discharge, reducing the overall volume of the monthly menstrual blood, reducing the duration of menstrual bleeding, reducing menstrual cramps and menstrual pain, and reducing the need for tampons and pads.

The invention thus provides a method of aspirating uterine fluid, comprising steps of providing a suction cup made of a medical-grade plastic and comprising a convex surface, the cup connected via said convex surface to a vacuum source; providing a vacuum valve or other means to ensure oscillating partial vacuum in said cup with a frequency of between 1 and 15 Hz, preferably between 3 and 12 Hz, such as between 4 and 10 Hz, for example between 5 and 9 Hz; providing an apparatus pushing and pulling said cup within a distance of up to 20 mm in each direction; inserting said cup into the vagina to be docked with the cervix; activating said oscillating vacuum, and simultaneously activating said apparatus, thereby causing cervix displacement of up to 20 mm, preferably with a frequency of up to 2.5 Hz; and extracting uterine fluid out of the vagina; thereby achieving at least one of the effects: providing the user with predetermined time intervals without menstrual discharge, reducing the overall volume of the monthly menstrual discharge, reducing the duration of menstrual bleeding, reducing menstrual cramps, reducing menstrual pain, and reducing the need for tampons and pads. In one preferred embodiment, at least in some of the working cycles the cup is attached by said vacuum pressure to the cervix and moves the surrounding tissue in the distal direction (away from the uterus), followed by interrupting the vacuum and releasing the tissue; this increases the efficiency of fluid extraction. The vacuum in the cup may be interrupted by a vacuum-release valve placed near to or on said convex surface.

In contrast with other known means of managing menses, the current method and device prevent the outflow of the menstrual fluid in predetermined future periods of time to ensure certain time intervals free of menstrual flow. The method is safe and easily employed by any instructed user, even without any expert supervision. The device of the invention introduces vacuum pressure and axial movements within a safe range for human tissue, verified by careful analysis and through authentic simulations on a model uterus.

The system and the method of the invention enable a woman in her menstrual period to better plan her activities and avoid inconvenient and embarrassing moments. The system and the device of the invention facilitate the reduction of the use of tampons and pads. The system of the invention ensures that the menstrual flow is collected in predetermined times. This invention provides women with predetermined time intervals free of menstrual flow.

The invention will be further described and illustrated by the following examples.

EXAMPLES

Figure 20:
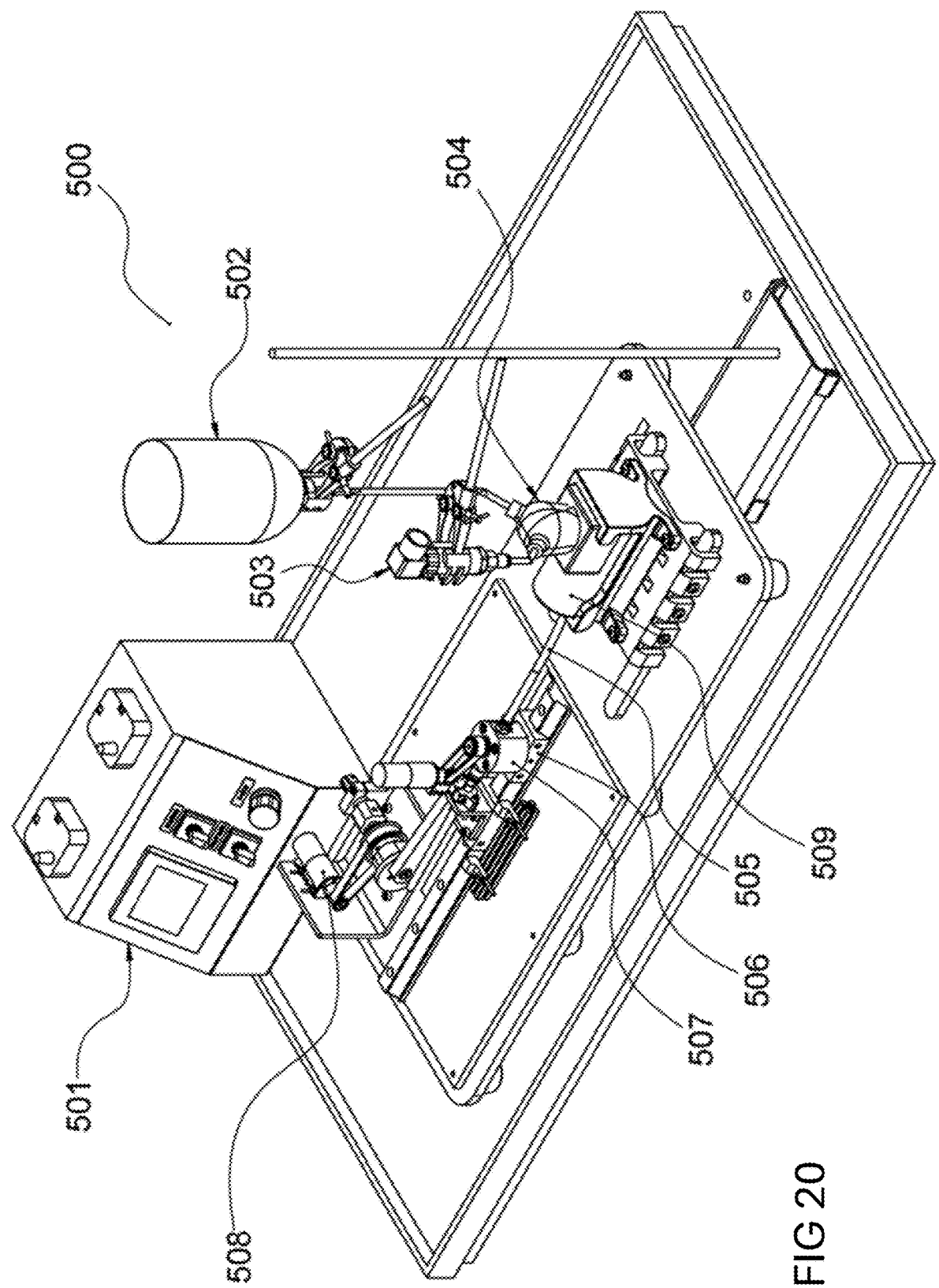
FIG. 20. illustrates a laboratory prototype of the device (500) according to one embodiment of the invention being tested on laboratory models of the uterus (504) and vagina (509). The unit is controlled by a processor—a controller and data logger (501), which controls a displacement-motor assembly (508) and a pressure oscillation valve assembly (507); the latter sits on the displacement carriage (506) and displaces the tube (505) which docks through the cup (not shown) with the cervix of the uterus model (504). Also shown are a uterine pressure sensor (503) and a menses silo (502) for simulating an internal uterine pressure of about 50 mbar.

Extraction of Menses Through Applying Oscillating Vacuum Pressure and Pull/Push Agitation to the Uterine Cervix—an Experimental Simulation Materials Parts and Materials in the Device and Models
- Void uterus models made of thermoplastic elastomer (TPE) with human-tissue-like properties (504 in FIG. 20);
- Plugs to seal the uterine orifice (cervical os) and filling ducts;
- Vaginal simulator (509 in FIG. 20);
- Empty water bottle connected to a plastic tube (502 in FIG. 20 to apply hydrostatic pressure through a pressure column);
- Water;
- Blood simulant (blood);
- Mucus simulant (wet and dried) to simulate tissue agglomerates of endometrial shed (endometrial shed);
- 10-ml syringe (syringe);
- Digital scale (scale);
- A prototype of the device used for extracting menses (blood and endometrial shed) from the uterus;
- Vacuum pump connected to a suction tube (505 in FIG. 20);
- Vacuum-pressure-adjustment valve;
- Cup connected to the suction tube;
- Vacuum-pressure-oscillation rotary valve (507 in FIG. 20) powered by a motor;
- Mechanism allowing axial movement of the cup (506 in FIG. 20) with respect to the cervix, powered by a motor (508 in FIG. 20);
- Two pressure sensors to measure the pressure in the canister and in the suction tube, in the vicinity of the cup; and
- Data logger (501 in FIG. 20).

Example 1

Comparing Models

Several models were prepared as follows. As seen in FIG. 20, a uterus model made of TPE, comprising a cavity, orifice (cervix) placed in a model vagina, a filling duct through which the model blood- or water-filling tubes are inserted, and another duct (usable for example for pressure measurement). The uterus model was mounted on a stand using a clamp so that the uterine body was perpendicular to the ground. Plugs were placed to seal the cervical os and pressure-measurement duct. The scale was placed just under the stand. An empty bowl was placed under the uterus to allow water collection. The tube connected to the bottle was inserted into said filling duct. The pressure column was filled with a fixed amount (600 g) of water. The plug sealing the cervical os was removed. The water was left to flow through the os into the bowl, while continuously measuring the mass of the drained water until the uterus was emptied, thereby characterizing different models. Some models were further used for extracting simulant menstrual fluid from the uterus as described below.

Example 2

Model Uterus Drainage

An endometrial-shed simulant designed to simulate menses (referred to as menses) comprising artificial mucus (wet endometrial shed) and pieces of artificial dried mucus (dried endometrial shed with dimensions of 10 mm×5 mm×5 mm) was prepared. The sucking cup, connected to the suction tube, was configured so to wrap the cervix. The rotary valve (507 in FIG. 20) controlled the oscillations of vacuum pressure produced by the vacuum pump; it had two working configurations, one for connecting the cup with vacuum and one for disconnecting it. In some embodiments, the cup is provided with a vacuum-release valve. Plugs were inserted into the cervical os and the pressure-measurement duct in order to seal them. Pieces of dried endometrial shed (imitation) with a total mass of ~3.5 g were inserted through the filling duct into the uterine cavity. The mass of the filled uterus was measured, and the mass of the dried endometrial shed contained in the uterine cavity was calculated as the difference between the current reading and that recorded before filling the uterus, with the aim of reaching any value between 3.25 g and 3.75 g. The syringe was washed and filled with ~3.5 g of wet endometrial shed, which was injected through the filling duct into the uterine cavity. The mass of the filled uterus was measured, and the mass of the endometrial shed contained in the uterine cavity (dried and wet) was calculated as the difference between the current reading and that recorded before filling the uterus, with the aim of reaching any value between 6.75 g and 7.25 g. The shed was packed towards the os by using centrifugal force. The plug sealing the cervical os was removed. The uterus was mounted on the vaginal simulator as seen in FIG. 20 so that the os was pointing 30 degrees below the horizon.

The flow rate of endometrial shed through the cervical os was measured in several model variants (a) to (c) as follows.

(a) Vacuum+uterine-pressure induced drainage: The flow rate of menses through the cervical os owing to gravitational forces, simulated uterine baseline pressure and vacuum pressure was measured. Vacuum suction was measured using digital pressure sensors (sampling rate: 2 Hz) connected to the suction canister and to the suction tube in the vicinity of the cup. The empty plastic tube connected to the empty bottle was inserted into the filling duct. The bottle (502 in FIG. 20) was filled with blood simulant so to create a ~50-cm blood column (with the aim of simulating intra-uterine pressure of ~5 kPa=50 mbar). The cup was placed so as to dock with the cervix, so that they were engaged with each other, without applying compression force. Vacuum pressure was applied to the cervix by the vacuum pump, via rotating the adjustment valve to the maximum. The magnitude and frequency of the vacuum pressure were set according to the required regimen. An example of the vacuum-pressure profile (oscillation wave) produced by the vacuum pump and rotary valve in the vicinity of the cup is shown on FIG. 21B for 1.1 Hz pressure oscillations, even though frequencies of 6.2 and 11.8 Hz were mostly used. The pressure magnitudes measured for several pressure oscillations are shown in Table 1.

TABLE 1

Peak vacuum pressures applied to the cervical os.

| Profile of vacuum pressure applied | Peak magnitude of nominal vacuum pump pressure [mbar] | Frequency of pressure oscillations [Hz] |
|---|---|---|
| Constant | 450-500 | 0 |
| Oscillating | 420-470 | 6.2 |
| Oscillating | 390-440 | 11.8 |

Measurement continued until all endometrial-shed simulant passed through the cervical os or for 30 min (the earlier of the two). The time points where endometrial shed was extracted were identified visually.

(b) Vacuum+pull-agitation+uterine-pressure induced drainage: The flow rate of menses through the cervical os owing to gravitational forces, simulated uterine baseline pressure, vacuum suction and gentle pulls applied to the cervix were explored. All pressure profiles listed in Table 1 were employed, while the cervix and cup were not constantly fully engaged, but strokes (of 15-mm magnitude, and 1.1-Hz or 2.5-Hz frequency) were applied by the device. Pulling the cup away from the cervix while applying vacuum pressure pulls the cervix distally together with the cup and occasionally creates a sudden loss of suction when the cup is disconnected from the cervix (thereby creating an effect of agitation similar to that applied by a rubber toilet plunger, where the cervix is being repeatedly pulled when the vacuum pressure is being built and released when the vacuum is released).

(c) Vacuum+pull-agitation+push-agitation+uterine-pressure induced drainage: The flow rate of menses through the cervical os owing to gravitational forces, simulated uterine baseline pressure, vacuum suction and gentle pulls and pushes alternatingly applied to the cervix in tandem, was measured. Since the same motor was used for applying both the pull and push agitations, these were always applied in the same frequency. The motor allowed a full stroke of 30 mm, which was divided between pull and push agitations of 15/15 mm.

All trials continued until all endometrial shed was drained or for 30 min (the earlier of the two). After the trial ended as 'successful' (all endometrial shed was drained, as indicated by the extraction of the shed blocking the os and the free flow of blood through the os) or 'unsuccessful' (by 30 min shed was still blocking the os), the mass of the uterus was measured, and the amount of drained endometrial shed was calculated as the difference between the current reading and that taken immediately before the extraction started. The procedure was repeated three times—once for each of three uterus models according to the combinations of vacuum pump pressure and strokes shown in Table 2.

TABLE 2

Details of vacuum pressure applied to the cervical os, and pull- and/or push- agitations applied to the cervix

| | Profile of vacuum pressure applied | Pressure oscillations frequency [Hz] | Push [mm] | Pull [mm] | Push/pull frequency [Hz] |
|---|---|---|---|---|---|
| 1a | Constant | N/A | No | No | N/A |
| 1b | Oscillating | 6.2 | No | No | N/A |
| 1c | Oscillating | 11.8 | No | No | N/A |
| 2a | Constant | N/A | No | 15 | 1.1 |
| 2b | Oscillating | 6.2 | No | 15 | 1.1 |
| 2c | Oscillating | 11.8 | No | 15 | 1.1 |
| 2d | Constant | N/A | No | 15 | 2.5 |
| 2e | Oscillating | 6.2 | No | 15 | 2.5 |
| 2f | Oscillating | 11.8 | No | 15 | 2.5 |
| 3a | Constant | N/A | 15 | 15 | 1.1 |
| 3b | Oscillating | 6.2 | 15 | 15 | 1.1 |
| 3c | Oscillating | 11.8 | 15 | 15 | 1.1 |
| 3d | Constant | N/A | 15 | 15 | 2.5 |
| 3e | Oscillating | 6.2 | 15 | 15 | 2.5 |
| 3f | Oscillating | 11.8 | 15 | 15 | 2.5 |

Results Evaluation

Below is Table 3, showing the scores of trials conducted for all combinations of magnitudes and frequencies of pressure and pull-push agitations, as described in Table 2.

TABLE 3

Summary of the results for the tests described in Table 2. Trial score is 1 if all fluid is drained after 5 min or less, 0.5 if all fluid is drained after 6 to 30 min, and 0 if it is not drained within 30 minutes.

| | Number of repetitions | Trial score | Mass fraction (%) of endometrial shed drained during the trial |
|---|---|---|---|
| 1a | 3 | 0, 0, 0 | 3%, 6%, 11% (mean: 7%) |
| 1b | 3 | 0, 0, 0 | 21%, 13%, 15% (mean: 17%) |
| 1c | 3 | 0, 1, 0 | 16%, 100%, 12% (mean: 42%) |
| 2a | 3 | 0, 0, 0 | 4%, 7%, 11% (mean: 7%) |
| 2b | 3 | 1, 0.5, 0 | 100%, 100%, 7% (mean: 68%) |
| 2c | 3 | 0, 0, 0 | 23%, 5%, 61% (mean: 30%) |
| 2d | 3 | 0, 0, 0 | 17%, 18%, 24% (mean: 19%) |
| 2e | 3 | 1, 1, 0 | 100%, 100%, 56% (mean: 85%) |
| 2f | 3 | 0, 1, 0 | 18%, 100%, 25% (mean: 48%) |
| 3a | 3 | 0, 0, 0.5 | 16%, 14%, 100% (mean: 42%) |
| 3b | 3 | 0, 1, 0 | 40%, 100%, 60% (mean: 67%) |
| 3c | 3 | 0, 0, 0 | 27%, 40%, 20% (mean: 29%) |
| 3d | 3 | 0, 1, 0 | 41%, 100%, 0% (mean: 47%) |
| 3e | 3 | 0, 0, 1 | 73%, 54%, 100% (mean: 75%) |
| 3f | 3 | 0, 0, 0.5 | 17%, 21%, 100% (mean: 45%) |

It could be seen that applying oscillating vacuum pressure to the cervix was generally more effective in extracting menses than constant pressure. When relying only on oscillating vacuum pump pressure (namely, without applying pull and/or push agitation), higher frequency of oscillations resulted in better performance. When combining pull agitation, or pull agitation simultaneously with push agitation, with oscillating vacuum pressure, lower frequency of pressure oscillations was more effective. The effect of pull agitation with vacuum (constant or oscillating) slightly contributed to the extraction of menses from the uterus. The frequency of pull agitation did not seem to affect the performance of the device. Combined pull-and-push agitation with vacuum pressure contributed to the extraction of menses from the uterus, but not more than pull agitation alone. High frequency of pull-and-push agitation resulted in better performance of the device.

It can be concluded that oscillating vacuum pressure is superior to constant pressure, with the more efficient extraction occurring when simultaneously employing cervical displacement.

Example 3

Another experiment simulating the suction of menstrual fluid from the uterus by applying vacuum pressure to the cervical os was conducted as follows. A TPE model of the uterus was filled with 8.00 to 8.25 g of artificial mucus simulating the menses (endometrial shed, only wet) and was mounted on a vaginal simulator. The uterus was then connected through one of its filling ducts to a bottle filled with blood simulant, so to create intrauterine pressure of 50 mbar. Vacuum pressure (of various pressures and frequencies, see Table 4) was applied to the model orifice (cervical os) so to drain the intrauterine menses through a flexible plastic cup connected to a pump suction canister. Pressure sensors connected to a data logger continuously measured (with a 2 Hz sampling rate) the pressure in the suction canister, as well as the pressure occurring inside the uterus or in the suction tube in the immediate vicinity of the cervix. The nominal vacuum pressure applied by the pump was constant or oscillating (with frequency of 5 or 9 Hz), reaching the maximum enabled by the system (420-500 mbar) or a pressure lower than this (300-400 mbar) (Table 4). The pump pressure was intermittently combined with an axial movement of the cup towards and/or away from the cervix, so to compress it or pull it; pulling the cup away from the cervix while applying vacuum pressure pulled the cervix distally together with the cup and occasionally created a sudden loss of suction when the cup was disconnected from the cervix. Push-pull agitations were applied in each of two frequencies (1.1 and 2.5 Hz) and three magnitudes (10, 15 and 20 mm, each side) (Table 4). In total, 34 combinations of magnitudes and frequencies of vacuum pressure and pull-push agitations were applied, in five blocks of tests (Table 4). Each of these was repeated three times. Each trial was assigned a score ranging between 0 to 1 depending on the time it took the menses to drain through the cup: 1—success after <3 min, 0.5—success after <15 min, 0.25—success after <30 min, 0—failure after >30 min. For each combination of pressure and agitation the mean score of the three trials was calculated. The results are shown in Table 4.

TABLE 4

Results of model tests

| | Pressure profile | Peak pressure magnitude [mbar] | Pressure oscillation Frequency [Hz] | Push [mm] | Pull [mm] | Push/pull frequency [Hz] | Mean score |
|---|---|---|---|---|---|---|---|
| 1 | Oscillating | 420-500 | 5 | No | No | N/A | 0.33 |
| 2 | Oscillating | 420-500 | 9 | No | No | N/A | 0.33 |
| 3 | Oscillating | 420-500 | 5 | 15 | 15 | 1.1 | 0.75 |
| 4 | Oscillating | 420-500 | 9 | 15 | 15 | 1.1 | 1.00 |
| 5 | Oscillating | 420-500 | 5 | 15 | 15 | 2.5 | 1.00 |
| 6 | Oscillating | 420-500 | 9 | 15 | 15 | 2.5 | 1.00 |
| 7 | Constant | 420-500 | N/A | 15 | 15 | 1.1 | 0.67 |
| 8 | Constant | 420-500 | N/A | 15 | 15 | 2.5 | 1.00 |
| 1 | Oscillating | 300-400 | 5 | No | No | N/A | 0.33 |
| 2 | Oscillating | 300-400 | 9 | No | No | N/A | 0.00 |
| 3 | Oscillating | 300-400 | 5 | 15 | 15 | 1.1 | 1.00 |
| 4 | Oscillating | 300-400 | 9 | 15 | 15 | 1.1 | 0.50 |
| 5 | Oscillating | 300-400 | 5 | 15 | 15 | 2.5 | 1.00 |
| 6 | Oscillating | 300-400 | 9 | 15 | 15 | 2.5 | 0.33 |
| 7 | Constant | 300-400 | N/A | 15 | 15 | 1.1 | 0.42 |
| 8 | Constant | 300-400 | N/A | 15 | 15 | 2.5 | 0.33 |
| 3 | Oscillating | 420-500 | 5 | 10 | 10 | 1.1 | 0.58 |
| 4 | Oscillating | 420-500 | 9 | 10 | 10 | 1.1 | 0.67 |
| 5 | Oscillating | 420-500 | 5 | 10 | 10 | 2.5 | 0.83 |
| 6 | Oscillating | 420-500 | 9 | 10 | 10 | 2.5 | 0.67 |
| 7 | Constant | 420-500 | N/A | 10 | 10 | 1.1 | 0.17 |
| 8 | Constant | 420-500 | N/A | 10 | 10 | 2.5 | 0.00 |
| 3 | Oscillating | 420-500 | 5 | 10 | 20 | 1.1 | 1.00 |
| 4 | Oscillating | 420-500 | 9 | 10 | 20 | 1.1 | 1.00 |
| 5 | Oscillating | 420-500 | 5 | 10 | 20 | 2.5 | 0.67 |
| 6 | Oscillating | 420-500 | 9 | 10 | 20 | 2.5 | 1.00 |
| 7 | Constant | 420-500 | N/A | 10 | 20 | 1.1 | 0.33 |
| 8 | Constant | 420-500 | N/A | 10 | 20 | 2.5 | 0.33 |
| 3 | Oscillating | 420-500 | 5 | No | 20 | 1.1 | 1.00 |
| 4 | Oscillating | 420-500 | 9 | No | 20 | 1.1 | 0.83 |
| 5 | Oscillating | 420-500 | 5 | No | 20 | 2.5 | 1.00 |
| 6 | Oscillating | 420-500 | 9 | No | 20 | 2.5 | 1.00 |
| 7 | Constant | 420-500 | N/A | No | 20 | 1.1 | 0.67 |
| 8 | Constant | 420-500 | N/A | No | 20 | 2.5 | 0.67 |

An increased magnitude of vacuum pressure generally resulted in more successful extraction of menses. Pressure oscillations also resulted in more successful drainage of menses when compared to the constant pressure. Pulling and pushing the cervix generally resulted in more successful drainage of menstrual fluid, with pulling and pushing by 15 mm being more successful than 10 mm.

It can be concluded that pressure oscillations are important for the extraction of menses; however, it is not necessarily beneficial to apply them in a frequency greater than 5 Hz. A higher amplitude of pressure oscillations is beneficial. Applying pull agitation ("toilet plunger effect") contributes to the effectiveness and efficiency of menses extraction, with or without push agitation. Increasing the frequency of the agitation (cervix displacement) is not necessarily beneficial.

While the invention has been described using some specific examples, many modifications and variations are possible. It is therefore understood that the invention is not intended to be limited in any way, other than by the scope of the appended claims.

The invention claimed is:

1. A device for aspirating uterine fluid, comprising
   i) a vacuum pump;
   ii) a suction tube having a first and a second end, connected with said pump via said first end, at least a part of the tube defining a linear axis;
   iii a suction cup connected with said tube via said second end and being wider than said tube, comprising an opening for aspirating said fluid, the cup and the tube being configured to be inserted into human vagina;
   iv) a noninvasive cervix-opening means, wherein said cervix-opening means comprises a vacuum regulation means providing application of vacuum;
   v) a liquid trap connected between said pump and said suction tube for holding said fluid; and
   vi) a processor for controlling the performance of said pump and said noninvasive cervix-opening means, and for storing software determining a device working regimen.

2. The device of claim 1, wherein said vacuum aspirates the vaginal and uterine fluid.

3. The device of claim 1, wherein said cervix-opening means further comprising an apparatus allowing a translational movement of said tube and said cup along said axis in each direction up to 40 mm, comprising an engine and an attachment member for connecting said suction tube with said engine.

4. The device of claim 3, wherein said translational movement results in moving said cup up to 20 mm in each direction, thereby causing displacement of said cervix.

5. The device of claim 1, wherein said cervix-opening means further comprising an apparatus supplying vibrations to the cervix during the vacuum aspiration.

6. The device of claim 1, wherein said processor and said noninvasive cervix-opening means provide application of vacuum which is repeated in the form of square waves or sawtooth waves.

7. The device of claim 1, wherein said cervix-opening means further comprising an apparatus supplying acoustic waves to the cervix.

8. The device of claim 1, further comprising one or more pressure sensors.

9. The device of claim 8, wherein said processor receives data from said sensors.

10. The device of claim 1, wherein said cup is made of a medical grade elastomer and comprises a surface being convex on a side of said suction tube.

11. The device of claim 1, wherein said suction tube and said cup are configured to adhere to the cervix, while aspirating said fluid.

12. The device of claim 1, further comprising a means for cutting blood clots or tissue shreds eventually present in said uterine fluid to smaller pieces before they enter to said suction tube.

13. The device of claim 1, wherein said pump provides a maximal negative pressure of between −150 and −750 mbar gauge and a maximal positive pressure of between 10 and 200 mbar gauge.

* * * * *